US012558015B2

(12) United States Patent
Krummen et al.

(10) Patent No.: US 12,558,015 B2
(45) Date of Patent: Feb. 24, 2026

(54) ENHANCED COMPUTATIONAL HEART SIMULATIONS

(71) Applicants: The Regents of the University of California, Oakland, CA (US); The Vektor Group Inc., San Diego, CA (US)

(72) Inventors: David Krummen, San Diego, CA (US); Christopher Villongco, San Diego, CA (US)

(73) Assignees: THE VEKTOR GROUP, INC., San Diego, CA (US); The Regents of the University of California, Oakland, CA (US)

( * ) Notice: Subject to any disclaimer, the term of this patent is extended or adjusted under 35 U.S.C. 154(b) by 973 days.

(21) Appl. No.: 17/418,642

(22) PCT Filed: Dec. 31, 2019

(86) PCT No.: PCT/US2019/069136
§ 371 (c)(1),
(2) Date: Jun. 25, 2021

(87) PCT Pub. No.: WO2020/142539
PCT Pub. Date: Jul. 9, 2020

(65) Prior Publication Data
US 2022/0061732 A1 Mar. 3, 2022

Related U.S. Application Data

(60) Provisional application No. 62/786,973, filed on Dec. 31, 2018.

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/349* (2021.01); *A61B 5/7264* (2013.01); *G16H 50/20* (2018.01)

(58) Field of Classification Search
CPC ........ G16H 50/20; A61B 5/361; A61B 5/349; A61B 5/7264
See application file for complete search history.

(56) References Cited

U.S. PATENT DOCUMENTS 5,273,038 A 12/1993 Beavin
6,370,412 B1 4/2002 Armoundas et al.
(Continued)

FOREIGN PATENT DOCUMENTS

CN 102917637 A 2/2013
JP 2013523344 A 6/2013
(Continued)

OTHER PUBLICATIONS

Aguado-Sierra, J., et al. "Patient-specific modeling of dyssynchronous heart failure: a case study." *Progress in Biophysics and Molecular Biology*, vol. 107 No. 1, 2011, pp. 147-155.
(Continued)

*Primary Examiner* — Steven G.S. Sanghera
(74) *Attorney, Agent, or Firm* — Perkins Coie LLP

(57) ABSTRACT

Methods to enhance the computational localization of cardiac arrhythmia sources are provided. A method may include receiving, from a first user, clinical data associated with a clinical case. The clinical data may include a patient anatomic information, diagnostic and/or treatment modalities, treatment parameters, treatment outcome, and medical literature. The clinical case may be indexed based on a first plurality of characteristics associated with the clinical data. The indexing may include associating at least a portion of the clinical data with a computational simulation of cardiac
(Continued)

arrhythmia having a second plurality of characteristics matching the first plurality of characteristics. At least a portion of the clinical data associated with the indexed case may be provided to a second user in response to a query from the user. Related systems and articles of manufacture are also provided.

14 Claims, 22 Drawing Sheets

(51) Int. Cl.
  *A61B 5/349*        (2021.01)
  *G16H 50/20*       (2018.01)

(56)                References Cited

U.S. PATENT DOCUMENTS

| | | | |
|---|---|---|---|
| 6,501,979 | B1 | 12/2002 | Manning et al. |
| 7,010,347 | B2 | 3/2006 | Schecter |
| 7,286,871 | B2 | 10/2007 | Cohen |
| 7,528,338 | B2 | 5/2009 | Ataka |
| 8,521,266 | B2 | 8/2013 | Narayan et al. |
| 9,211,110 | B2 | 12/2015 | Rubin et al. |
| 9,277,970 | B2 | 3/2016 | Mansi et al. |
| 9,706,935 | B2 | 7/2017 | Spector |
| 10,315,144 | B2 | 6/2019 | Reichter et al. |
| 10,556,113 | B2 | 2/2020 | Villongco et al. |
| 10,713,791 | B2 | 7/2020 | Krummen et al. |
| 10,856,816 | B2 | 12/2020 | Villongco |
| 11,344,263 | B2 | 5/2022 | Villongco |
| 2002/0035334 | A1 | 3/2002 | Meij et al. |
| 2004/0015081 | A1 | 1/2004 | Kramer et al. |
| 2004/0176697 | A1 | 9/2004 | Kappenberger et al. |
| 2007/0016108 | A1 | 1/2007 | Bewlay et al. |
| 2007/0032733 | A1 | 2/2007 | Burton |
| 2007/0219452 | A1 | 9/2007 | Cohen et al. |
| 2007/0259031 | A1 | 11/2007 | Bankiewicz et al. |
| 2007/0270703 | A1 | 11/2007 | He et al. |
| 2007/0276270 | A1 | 11/2007 | Tran |
| 2008/0021336 | A1 | 1/2008 | Dobak |
| 2008/0077032 | A1 | 3/2008 | Holmes et al. |
| 2008/0167567 | A1 | 7/2008 | Bashour |
| 2008/0188762 | A1 | 8/2008 | John |
| 2009/0306732 | A1 | 12/2009 | Rosenberg et al. |
| 2010/0016917 | A1 | 1/2010 | Efimov et al. |
| 2010/0152796 | A1 | 6/2010 | Schecter |
| 2010/0280355 | A1 | 11/2010 | Grimm et al. |
| 2010/0298904 | A1 | 11/2010 | Blomqvist et al. |
| 2011/0251504 | A1 | 10/2011 | Tereshchenko et al. |
| 2011/0251505 | A1* | 10/2011 | Narayan .............. A61B 5/7264 |
| | | | 600/515 |
| 2011/0307231 | A1 | 12/2011 | Kirchner et al. |
| 2011/0311116 | A1 | 12/2011 | Benn |
| 2012/0035459 | A1 | 2/2012 | Revishvili et al. |
| 2012/0087563 | A1 | 4/2012 | Lonasec et al. |
| 2012/0165674 | A1 | 6/2012 | Abe et al. |
| 2012/0283587 | A1 | 11/2012 | Gosh et al. |
| 2013/0006131 | A1 | 1/2013 | Narayan et al. |
| 2013/0034203 | A1 | 2/2013 | Wang et al. |
| 2013/0096394 | A1 | 4/2013 | Gupta et al. |
| 2013/0131529 | A1 | 5/2013 | Jia et al. |
| 2013/0158557 | A1 | 6/2013 | Komistek |
| 2013/0197881 | A1 | 8/2013 | Mansi et al. |
| 2013/0211256 | A1 | 8/2013 | Russell et al. |
| 2014/0005562 | A1 | 1/2014 | Bunch et al. |
| 2014/0088943 | A1 | 3/2014 | Trayanova et al. |
| 2014/0107510 | A1 | 4/2014 | Bogun et al. |
| 2014/0200575 | A1 | 7/2014 | Spector |
| 2014/0241988 | A1 | 8/2014 | Jalife |
| 2014/0276152 | A1 | 9/2014 | Narayan et al. |
| 2014/0323882 | A1 | 10/2014 | Ghosh et al. |
| 2014/0329907 | A1 | 11/2014 | Ye |
| 2015/0042646 | A1 | 2/2015 | Comaniciu et al. |
| 2015/0216432 | A1 | 8/2015 | Yang |
| 2015/0216434 | A1 | 8/2015 | Ghosh et al. |
| 2015/0216438 | A1 | 8/2015 | Bokan et al. |
| 2015/0294082 | A1 | 10/2015 | Passerini et al. |
| 2015/0313510 | A1 | 11/2015 | Razavi et al. |
| 2016/0005106 | A1 | 1/2016 | Giraldez et al. |
| 2016/0012592 | A1 | 1/2016 | Chou et al. |
| 2016/0022375 | A1 | 1/2016 | Blake et al. |
| 2016/0135702 | A1 | 5/2016 | Perez |
| 2016/0157769 | A1 | 6/2016 | Min et al. |
| 2016/0210435 | A1 | 7/2016 | Neumann et al. |
| 2016/0262635 | A1 | 9/2016 | McCullouch et al. |
| 2016/0331337 | A1 | 11/2016 | Ben-Haim |
| 2017/0027649 | A1 | 2/2017 | Kiraly et al. |
| 2017/0079542 | A1 | 3/2017 | Spector |
| 2017/0161896 | A1 | 6/2017 | Blake, III |
| 2017/0178403 | A1* | 6/2017 | Krummen .............. A61B 5/361 |
| 2017/0185740 | A1 | 6/2017 | Seegerer et al. |
| 2017/0209698 | A1 | 7/2017 | Villongco et al. |
| 2017/0304005 | A1 | 10/2017 | Maino et al. |
| 2017/0319278 | A1 | 11/2017 | Trayanova et al. |
| 2017/0367603 | A1 | 12/2017 | Spector |
| 2018/0028265 | A1 | 2/2018 | Azevedo Da Silva et al. |
| 2018/0028828 | A1 | 2/2018 | Cao et al. |
| 2018/0055401 | A1 | 3/2018 | Wang et al. |
| 2018/0318606 | A1 | 11/2018 | Robinson et al. |
| 2019/0104951 | A1 | 4/2019 | Valys et al. |
| 2019/0206127 | A1 | 7/2019 | Krummen et al. |
| 2019/0282821 | A1 | 9/2019 | Masuda et al. |
| 2019/0304183 | A1 | 10/2019 | Krummen et al. |
| 2019/0328335 | A1 | 10/2019 | Villongco |
| 2019/0333643 | A1* | 10/2019 | Villongco .............. A61B 5/319 |
| 2020/0138394 | A1 | 5/2020 | Vanden Berghe et al. |
| 2020/0245935 | A1 | 8/2020 | Krummen et al. |

FOREIGN PATENT DOCUMENTS

| | | |
|---|---|---|
| WO | WO-2004102482 A1 | 11/2004 |
| WO | WO-2005072607 A1 | 8/2005 |
| WO | WO-2009079344 A1 | 6/2009 |
| WO | WO-2010042826 A1 | 4/2010 |
| WO | WO-2010052303 A1 | 5/2010 |
| WO | WO-2010054409 A1 | 5/2010 |
| WO | WO-2012055498 A1 | 5/2012 |
| WO | WO-2012109618 A2 | 8/2012 |
| WO | 2017112910 A1 | 6/2017 |

OTHER PUBLICATIONS

Alexander, D. C., et al. "Spatial Transformations of Diffusion Tensor Magnetic Resonance Images." *IEEE Transactions on Medical Imaging*, vol. 20 No. 11, 2001, pp. 1131-1139.

Aronszajn, N. "Theory of reproducing kernels." *Transactions of the American Mathematical Society*, vol. 68, 1950, pp. 337-404.

Arsigny, V., et al. "Log-Euclidean metrics for fast and simple calculus on diffusion tensors." Magnetic Resonance in Medicine : Official Journal of the Society of Magnetic Resonance in Medicine / Society of Magnetic Resonance in Medicine, vol. 56 No. 2, 2006, pp. 411-421.

Auricchio, A., et al. "Characterization of left ventricular activation in patients with heart failure and left bundle-branch block." *Circulation*, vol. 109, No. 9, 2004, pp. 1133-1139.

Bazan, V., et al., "Three-dimensional myocardial scar characterization from the endocardium: Usefulness of endocardial unipolar electroanatomic mapping." J Cardiovasc Electrophysiol 2019;30:427-437.

Berger, T., et al."Single-beat noninvasive imaging of cardiac electrophysiology of ventricular pre- excitation." *Journal of the American College of Cardiology*, vol. 48, No. 10, 2006, pp. 2045-2052.

Burger, H. C., et al., "Heart-Vector and Leads." British Heart Journal, vol. 8, No. 3, 1946, pp. 157-161.

Cao, Y., et al. "Large deformation diffeomorphic metric mapping of vector fields." *Medical Imaging, IEEE Transactions*, vol. 24, No. 9, 2005, pp. 1216-1230.

(56)                 References Cited

OTHER PUBLICATIONS

Carrault, G., et al., "A model-based approach for learning to identify cardiac arrhythmias." Joint European Conference on Artificial Intelligence in Medicine and medical Decision Making. Springer, Berlin, Heidelberg, 1999. (Year: 1999).

Carrault, G., et al., "Temporal abstraction and inductive logic programming for arrhythmia recognition from electrocardigrams." Artificial intelligence in medicine 28.3 (2003): 231-263. (Year: 2003).

Chalil, S., et al., "Intraventricular Dyssynchrony Predicts Mortality and Morbidity After Cardiac Resynchronization Therapy A Study Using Cardiovascular Magnetic Resonance Tissue Synchronization Imaging", Journal of The American College Of Cardiology, vol. 50, No. 3, pp. 243-252, XP029654014, ISSN: 0735-1097, DOI: 10.1016/J.JACC. 2007.03.035.

Cluitmans, M. J. M., et al. "Inverse Reconstruction of Epicardial Potentials Improve by Vectorcardiography and Realistic Potentials." *Computing in Cardiology*, vol. 40, 2013, pp. 369-372.

Cobb, L.A., et al., "Changing incidence of out-of-hospital ventricular fibrillation, 1980-2000." Jama 288.23 (2002): 3008-3013.

Coronel, R., et al., "Right ventricular fibrosis and conduction delay in a patient with clinical signs of Brugada syndrome: a combined electrophysiological, genetic, histopathologic, and computational study." Circulation. 2005;112:2769-77.

Cortez, D.L. et al., "When deriving the spatial QRS-T angle from the 12-lead electrocardiogram, which transform is more Frank: regression or inverse Dower?" Journal of Electrocardiology 43.4 (2010): 302-309.

Daubert, J.-C., et al. "2012 EHRA/HRS expert consensus statement on cardiac resynchronization therapy in heart failure: implant and follow-up recommendations and management." *Heart Rhythm : The Official Journal of the Heart Rhythm Society*, vol. 9 No. 9, 2012, pp. 1524-1576.

De Boeck, B.W.L., et al., "Septal rebound stretch reflects the functional substrate to cardiac resynchronization therapy and predicts volumetric and neurohormonal response." Eur J Heart Fail. 2009;1 1(9):863-71, 9 pages.

De Vito, E., et al. "Adaptive kernel methods using the balancing principle." *Foundations of Computational Mathematics*, vol. 10, No. 4, 2010, pp. 455-479.

De Vito, E., et al. "Learning from examples as an inverse problem." *Journal of Machine Learning Research*, vol. 6, 2005, pp. 883-904.

Dossel, O., et al. "Imaging of bioelectric sources in the heart using a cellular automaton model." *Conference Proceedings : Annual International Conference of the IEEE Engineering in Medicine and Biology Society. IEEE Engineering in Medicine and Biology Society. Conference*, 2005, pp. 1067-1070.

Edenbrandt, L., et al., "Vectorcardiogram synthesized from a 12-lead ECG: superiority of the inverse Dower matrix." Journal of Electrocardiology, vol. 21, No. 4, 1988, pp. 361-367.

Engl, H., et al. "Regularization of Inverse Problems." *Mathematics and Its Application*, vol. 375, 1996.

Epstein A.E., et al., ACC/AHA/HRS 2008 Guidelines for Device-Based Therapy of Cardiac Rhythm AbnormalitiesPractice Guideline. J Am Coll Cardiol. 2008;51:21.

Epstein A.E., et al., American College of Cardiology F, American Heart Association Task Force on Practice G and Heart Rhythm S. 2012 ACCF/AHA/HRS focused update incorporated into the ACC/AHA/HRS 2008 guidelines for device-based therapy of cardiac rhythm abnormalities: a report of the American College of Cardiology Foundation/American Heart Association Task Force on Practice Guidelines and the Heart Rhythm Society. J Am Coll Cardiol. 2013;61:e6-75.

Fillard, P., et al., "Clinical DT-MRI estimation, smoothing, and fiber tracking with log-Euclidean metrics." IEEE Transactions on Medical Imaging, vol. 26, No. 11, 2007, pp. 1472-1482.

Gersh B.J., et al., 2011 ACCF/AHA Guideline for the Diagnosis and Treatment of Hypertrophic Cardiomyopathy: a report of the American College of Cardiology Foundation/American Heart Association Task Force on Practice Guidelines. Developed in collaboration with the American Association for Thoracic Surgery, American Society of Echocardiography, American Society of Nuclear Cardiology, Heart Failure Society of America, Heart Rhythm Society, Society for Cardiovascular Angiography and Interventions, and Society of Thoracic Surgeons. Journal of the American College of Cardiology. 2011;58:e212-60.

Gold, M. R., et al. "The relationship between ventricular electrical delay and left ventricular remodelling with cardiac resynchronization therapy." *European Heart Journal*, vol. 32, No. 20, 2011, pp. 2516-2524.

Golub, G. H., et al., "Singular Value Decomposition and Least Squares Solutions." Numerische Mathematik, vol. 14, 1970, pp. 403-420.

Gonzales, M. J., et al. "A three-dimensional finite element model of human atrial anatomy: new methods for cubic Hermite meshes with extraordinary vertices." *Medical Image Analysis*, vol. 17 No. 5, 2013, pp. 525-537.

Gonzales, M.J., et al., "Structural contributions to fibrillatory rotors in a patient-derived computational model of the atria." EP Europace 16.suppl 4 (2014): iv3-iv10.

Greensite, F., et al., "An improved method for estimating epicardial potentials from the body surface." IEEE Transactions on Bio-Medical Engineering, vol. 45, No. 1, 1998, pp. 98-104.

Guillem, M. S., et al. "Derivation of orthogonal leads from the 12-lead ECG. Accuracy of a single transform for the derivation of atrial and ventricular waves." In Computers in Cardiology, 2006, pp. 249-252.

Gulrajani, R.M., The forward and inverse problems of electrocardiograma IEEE Engineering in Medicine and Biology Magazine 17.5 (1998): 84-101.

Haissaguerre, M., et al., "Localized Structural Alterations Underlying a Subset of Unexplained Sudden Cardiac Death." Circ Arrhythm Electrophysiol 2018; 11:e006120.

Han, C., et al. "Noninvasive reconstruction of the three-dimensional ventricular activation sequence during pacing and ventricular tachycardia in the canine heart." *American Journal of Physiology. Heart and Circulatory Physiology*, vol. 302, No. 1, 2012, pp. H244-H252.

Han, C., et al. "Noninvasive reconstruction of the three-dimensional ventricular activation sequence during pacing and ventricular tachycardia in the rabbit heart." *Conference Proceedings : Annual International Conference of the IEEE Engineering in Medicine and Biology Society*,2011, pp. 1684-1687.

He, B., et al. "Noninvasive three-dimensional activation time imaging of ventricular excitation by means of a heart-excitation model." *Physics in Medicine and Biology*, vol. 47, No. 22, 2002, pp. 4063-4078.

Helm, R.H., et al., "Cardiac Dyssynchrony Analysis Using Circumferential Versus Longitudinal Strain: Implications for Assessing Cardiac Resynchronization." Circulation. 111 (2005), pp. 2760-2767, 8 pages.

Ho, G., et al., "Rotors exhibit greater surface ECG variation during ventricular fibrillation than focal sources due to wavebreak, secondary rotors, and meander." J Cardiovasc Electrophysiol. 2017;28:1158-1166.

Actually Hren Do Not Cite in an IDS—Horacek, B.M., "Value of simulated body surface potential maps as templates in localizing sites of ectopic activation for; radiofrequency ablation." Physiological measurement 18.4 (1997): 373. (Year: 1997).

Hren, R., et al., "Value of simulated body surface potential maps as templates in localizing sites of ectopic activation for radiofrequency ablation." Physiological measurement 18.4 (1997): 373-400.

Kerckhoffs, R., et al., "Ventricular dilation and electrical dyssynchrony synergistically increase regional mechanical non-uniformity but not mechanical dyssynchrony: a computational model." Circulation: Heart Failure (2010): Circheartfailure—109.

Kimeldorf, G., et al., "Some results on Tchebycheffian spline functions." Journal of Mathematical Analysis and Applications, vol. 33, 1971, pp. 82-95.

Kindermann, S., et al., "On the convergence of the quasi-optimality criterion for (iterated) Tikhonov regularization." Inverse Problems and Imaging, vol. 2, No. 2, 2008, pp. 291-299.

(56)           References Cited

OTHER PUBLICATIONS

Kirn, Borut, et al., "Mechanical discoordination rather than dyssynchrony predicts reverse remodeling upon cardiac resynchronization." Am J Physiol Heart Circ Physiol. 295, Aug. 2008;295(2):H640-6, 7 pages.

Kors, J. A., et al. "Reconstruction of the Frank vectorcardiogram from standard electrocardiogra leads: diagnostic comparison of different methods." *European Heart Journal*, vol. 11, No. 12, 1990, pp. 1083-1092.

Krishnamurthy, A., et al., "CRT Response is Greater in Patients With Larger Fraction of the Myocardium Performing Negative Regional Work." Circulation 128.Suppl 22 (2013): A11135-A11135, Abstract only.

Krishnamurthy, A., et al., "Patient-specific models of cardiac biomechanics." Journal of computational physics 244 (2013): 4-21.

Krummen, D.E., et al., "Mechanisms of human atrial fibrillation initiation: clinical and computational studies of repolarization restitution and activation latency." Circ Arrhythm Electrophysiol 2012;5:1149-59.

Krummen, D.E., et al., "Modifying Ventricular Fibrillation by Targeted Rotor Substrate Ablation: Proof-of-Concept from Experimental Studies to Clinical VF." J Cardiovasc Electrophysiol 2015;26:1117-26.

Krummen, D.E., et al., "Rotor stability separates sustained ventricular fibrillation from self-terminating episodes in humans." Journal of the American College of Cardiology 63.24 (2014): 2712-2721.

Leclercq, C., et al., "Systolic Improvement and Mechanical Resynchronization Does Not Require Electrical Synchrony in the Dilated Failing Heart With Left Bundle-Branch Block." Circulation, 106 (2002). pp. 1760-1763, 4 pages.

Li, G., et al., "Localization of the site of origin of cardiac activation by means of a heart-model-based electrocardiogramaging approach." IEEE Transactions on Bio-Medical Engineering, vol. 48, No. 6, 2001, pp. 660-669.

Lin, T., et al. "Implant electrical characteristics predict response to cardiac resynchronization therapy." *World Journal of Cardiovascular Diseases*, 2014.

Liu, C., et al. "Estimation of global ventricular activation sequences by noninvasive 3-dimensional electrical imaging: validation studies in a swine model during pacing." *Journal of Cardiovasc Electrophysiol*, vol. 19, No. 5, 2009, pp. 535-540.

McVeigh, E.R., et al., "Regional myocardial strain measurements from 4DCT in patients with normal LV function." J Cardiovasc Comput Tomogr 2018;12:372-378.

Messinger-Rapport, B. J., et al., "Regularization of the inverse Problem in Electrocardiograma Model Study." Mathematical Biosciences, vol. 89, 1998, pp. 79-118.

Messnarz, B., et al., "A new spatiotemporal regularization approach for reconstruction of cardiac transmembrane potential patterns." IEEE transactions on Biomedical Engineering 51.2 (2004): 273-281.

Micchelli, C. A., et al., "Learning the kernel function via regularization." Journal of Machine Learning Research, vol. 6, 2005, pp. 1099-1125.

Myerburg R.J., et al., "Interpretation of outcomes of antiarrhythmic clinical trials: design features and population impact." Circulation. 1998;97:1514-21.

Narayan, S.M., et al., "Steep restitution of ventricular action potential duration and conduction slowing in human Brugada syndrome." Heart Rhythm. 2007;4:1087-9.

Nash, M.P., et al., "Evidence for multiple mechanisms in human ventricular fibrillation." Circulation 114.6 (2006): 536-542.

Naumova, V., et al. "A meta-learning approach to the regularized learning—case study: Blood glucose prediction." *Neural Networks*, vol. 33, 2012, pp. 181-193.

Naumova, V., et al. "Extrapolation in variable RKHSs with application to the blood glucose reading." *Inverse Problems*, vol. 27, No. 7, 2011, pp. 1-13.

Niederer, S.A., et al., "Analyses of the Redistribution of Work following Cardiac Resynchronisation Therapy in a Patient Specific Model." PLoS One 7(8), 2012, 9 pages.

O'Hanlon, R., et al., "Prognostic significance of myocardial fibrosis in hypertrophic cardiomyopathy." Journal of the American College of Cardiology. 2010;56:867-74.

Oster, H.S., et al., "Noninvasive electrocardiogramaging: reconstruction of epicardial potentials, electrograms, and isochrones and localization of single and multiple electrocardiac events." Circulation. 1997;96:1012-24.

Oster, H. S., et al., "The use of temporal information in the regularization of the inverse problem of electrocardiography." IEEE Transactions on Bio-Medical Engineering, vol. 39, No. 1, 1992, pp. 65-75.

Pfeifer, B., et al. "Patient-specific volume conductor modeling for non-invasive imaging of cardiac electrophysiology." *uThe Open Medical Informatics Journal*, vol. 2, 2008, pp. 32-41.

Ploux, S., et al. "Noninvasive electrocardiogramapping to improve patient selection for cardiac resynchronization therapy: beyond QRS duration and left bundle branch block morphology." *Journal of the American College of Cardiology*, vol. 61, No. 24, 2013, pp. 2435-2443.

Ramanathan, C., et al. "Noninvasive electrocardiogramaging for cardiac electrophysiology and arrhythmia." *Nature Medicine*, vol. 10, No. 4, 2004, pp. 422-428.

Ramanathan, C., et al. "Noninvasive Electrocardiogramaging (ECGI): Application of the Generalized Minimal Residual (GMRes) Method." Annals of Biomedical Engineering, vol. 31, No. 8, 2003, pp. 981-994.

Rodriguez, L.-M., et al. "Variable patterns of septal activation in patients with left bundle branch block and heart failure." Journal of Cardiovascular Electrophysiology, vol. 14, No. 2, 2003, pp. 135-141.

Rotter, M., et al. "Reduction of fluoroscopy exposure and procedure duration during ablation of atrial fibrillation using a novel anatomical navigation system." *European Heart Journal*, vol. 26, No. 14, 2005, pp. 1415-1421.

Rudy, Y. "Noninvasive electrocardiogramaging of arrhythmogenic substrates in humans." Circulation Research, vol. 112, No. 5, 2013, pp. 863-874.

Schreck, D. M., et al. "Statistical methodology: VI. Mathematical modeling of the electrocardiogram using factor analysis." *Academic Emergency Medicine*, vol. 5, No. 9, 1998, pp. 929-934.

Seo, Y., et al., "Mechanical dyssynchrony assessed by speckle tracking imaging as a reliable predictor of acute and chronic response to cardiac resynchronization therapy." Journal of the American Society of Echocardiography 22.7 (2009): 839-846.

Singh, J. P., et al. "Left ventricular lead electrical delay predicts response to cardiac resynchronization therapy." *Heart Rhythm*, vol. 3, No. 11, 2006, pp. 1285-1292.

Stecker, E.C., et al., "Population-based analysis of sudden cardiac death with and without left ventricular systolic dysfunction: two-year findings from the Oregon Sudden Unexpected Death Study." J Am Coll Cardiol. 2006;47:1161-6.

Stevenson, W.G., et al., "Identification of reentry circuit sites during catheter mapping and radiofrequency ablation of ventricular tachycardia late after myocardial infarction." Circulation 1993;88:1647-70.

Strauss, D. G., et al. "Defining left bundle branch block in the era of cardiac resynchronization therapy." *The American Journal of Cardiology*, vol. 107, No. 6, 2011, pp. 927-934.

Sweeney, M. O., et al. "Analysis of ventricular activation using surface electrocardiograma predict left ventricular reverse volumetric remodeling during cardiac resynchronization therapy." *Circulation*, vol. 121, No. 5, 2010, pp. 626-634.

Taggart, P., et al. "Developing a novel comprehensive framework for the investigation of cellular and whole heart electrophysiology in the in situ human heart: Historical perspectives, current progress and future prospects." Progress in biophysics and molecular biology 115. 2-3 (2014): 252-260.

Ten Tusscher, K. H. W. J., et al., "A model for human ventricular tissue." American Journal of Physiology-Heart and Circulatory Physiology 286.4 (2004): H1573-H1589.

(56)                    References Cited

OTHER PUBLICATIONS

Ten Tusscher, K.H.W.J., et al., "Alternans and spiral breakup in a human ventricular tissue model. American Journal of Physiology." Heart and Circulatory Physiology, vol. 291,2006, pp. H1088-H1100.

Tikhonov, A. N., et al. *Solutions of ill-posed problems.* Winston, (p. 258), 1997.

Tikhonov, A. N., et al., "Use of the regularization methods in non-linear problems." USSR Computational Mathematics and Mathematical Physics, vol. 5, 1965.

Tobon, C., et al., "Dominant frequency and organization index maps in a realistic three-dimensional computational model of atrial fibrillation." Europace 14.suppl 5 (2012): v25-v32.

Vadakkumpadan, F., et al. "Image-based estimation of ventricular fiber orientations for personalized modeling of cardiac electrophysiology." *Medical Imaging, IEEE Transactions*, vol. 31, No. 5, 2012, pp. 1051-1060.

Van der Graaf, A. W. M., et al. "Noninvasive imaging of cardiac excitation: current status and future perspective. Annals of Noninvasive Electrocardiology." *The Official Journal of the International Society for Holter and Noninvasive Electrocardiology, Inc*, vol. 19, No. 2, 2014, pp. 105-113.

Van Deursen, C. J., et al. "Vectorcardiography as a tool for easy optimization of cardiac resynchronization therapy in canine left bundle branch block hearts." *Circulation: Arrhythmia and Electrophysiology*, vol. 5, No. 3, 2012, pp. 544-552.

Vaquero, M., et al. "Cardiac Fibrillation: From Ion Channels to Rotors in the Human Heart." *Heart Rhythm : The Official Journal of the Heart Rhythm Society*, vol. 5, No. 6, 2008, pp. 872-879.

Varma, N., et al. "Electrocardiogramaging of patients with heart failure with left bundle branch block and response to cardiac resynchronization therapy." *Journal of Electrocardiology*, vol. 40,2007, pp. S174-S178.

Villongco, C. T., et al. "Patient-specific modeling of ventricular activation pattern using surface ecg-derived vectorcardiogram in bundle branch block." *Progress in Biophysics and Molecular Biology*, vol. 115, No. 2, 2014, pp. 305-313.

Wang, Y., et al. "Noninvasive electroanatomic mapping of human ventricular arrhythmias with electrocardiogramaging." *Science Translational Medicine*, vol. 3, No. 98, 2011, pp. 98ra84.

Wittkampf, F. H., et al. "LocaLisa new technique for real-time 3-dimensional localization of regular intracardiac electrodes." *Circulation*, vol. 99, No. 10, 1999, pp. 1312-1317.

Yamashita, Y. "Theoretical studies on the inverse problem in electrocardiogramand the uniqueness of the solution." *Biomedical Engineering, IEEE Transactions*, vol. 11, 1982, pp. 719-725.

Yokokawa, M. et al., "Automated analysis of the 12-lead electrocardiogram to identify the exit site of prostinfarction ventricular tachycardia." Heart Rhythm Society vol. 9, No. 3, Mar. 2012: 330-334, (5 pages).

Yushkevich, P. A., et al. "User-guided 3D active contour segmentation of anatomical structures: significantly improved efficiency and reliability." *NeuroImage*, vol. 31, No. 3, 2006, pp. 1116-1128.

Zhang, J., et al., "Cardiac electrophysiological substrate underlying the ECG phenotype and electrogram abnormalities in Brugada syndrome patients." Circulation. 2015;131:1950-9.

Zhang, X., et al. "Noninvasive three-dimensional electrocardiogramaging of ventricular activation sequence." *AJP—Heart Circulatory Physiology*, vol. 289, 2005, pp. 2724-2732.

International Search Report and Written Opinion issued in International Application No. PCT/US2019/069136, mailed May 11, 2020, (May 22, 2020). 13 pages.

Office Action issued for U.S. Appl. No. 17/081,735, mailed Aug. 2, 2021, 29 pages.

Office Action issued for U.S. Appl. No. 17/081,735, mailed Aug. 30, 2021, 18 pages.

Notice of Allowance issued for U.S. Appl. No. 17/081,735, mailed Feb. 2, 2022, 23 pages.

Supplementary European Search Report issued in European Application No. 19906798.4-1113, mailed Aug. 17, 2022, 9 pages.

Man, S.-C et al., "Reconstruction of standard 12-lead electrocardigrams from 12-lead electrocardiograms recorded with the Mason-Likar electrode configuration," Journal of Electrocardiology, vol. 14 (2008), pp. 211-219.

Extended European Search Report issued in European Application No. 19831553.3-1113, mailed Mar. 3, 2022, 9 pages.

* cited by examiner

310

320

330

600

620

600

SOURCE OF
CARDIAC
ARRHYTHMIA

PACING SITES

700

700

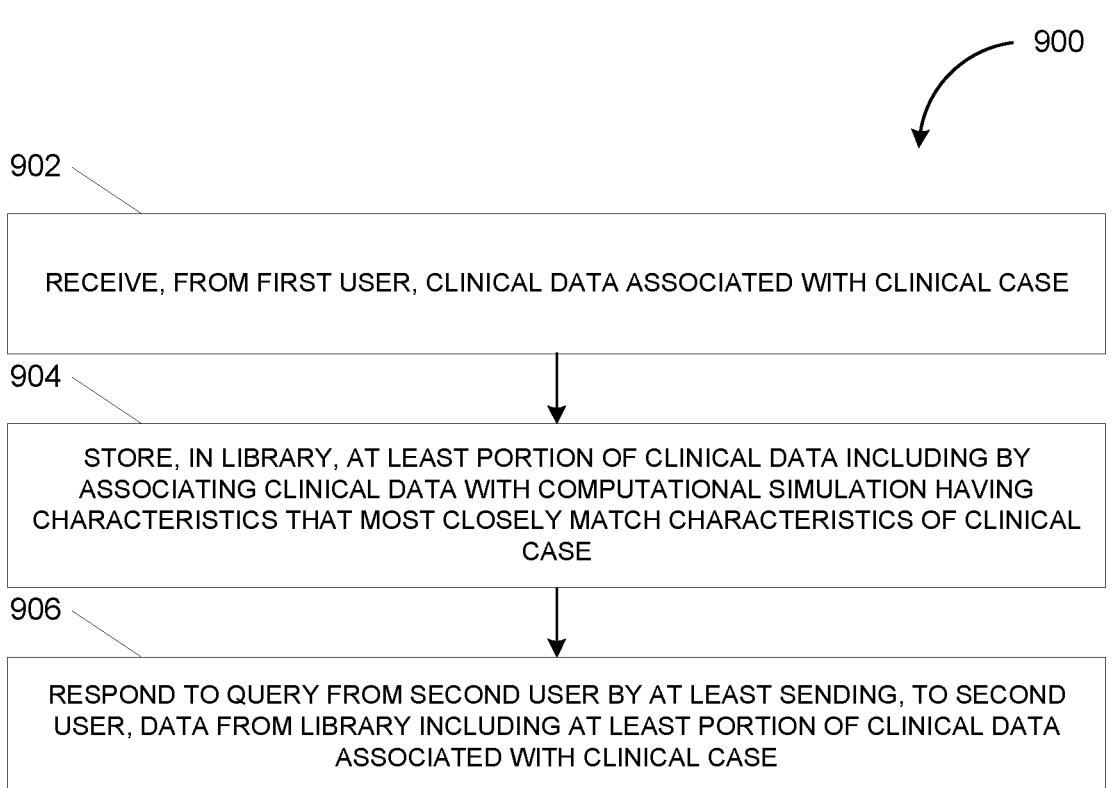

900

902

RECEIVE, FROM FIRST USER, CLINICAL DATA ASSOCIATED WITH CLINICAL CASE

904

STORE, IN LIBRARY, AT LEAST PORTION OF CLINICAL DATA INCLUDING BY ASSOCIATING CLINICAL DATA WITH COMPUTATIONAL SIMULATION HAVING CHARACTERISTICS THAT MOST CLOSELY MATCH CHARACTERISTICS OF CLINICAL CASE

906

RESPOND TO QUERY FROM SECOND USER BY AT LEAST SENDING, TO SECOND USER, DATA FROM LIBRARY INCLUDING AT LEAST PORTION OF CLINICAL DATA ASSOCIATED WITH CLINICAL CASE

FIG. 9A

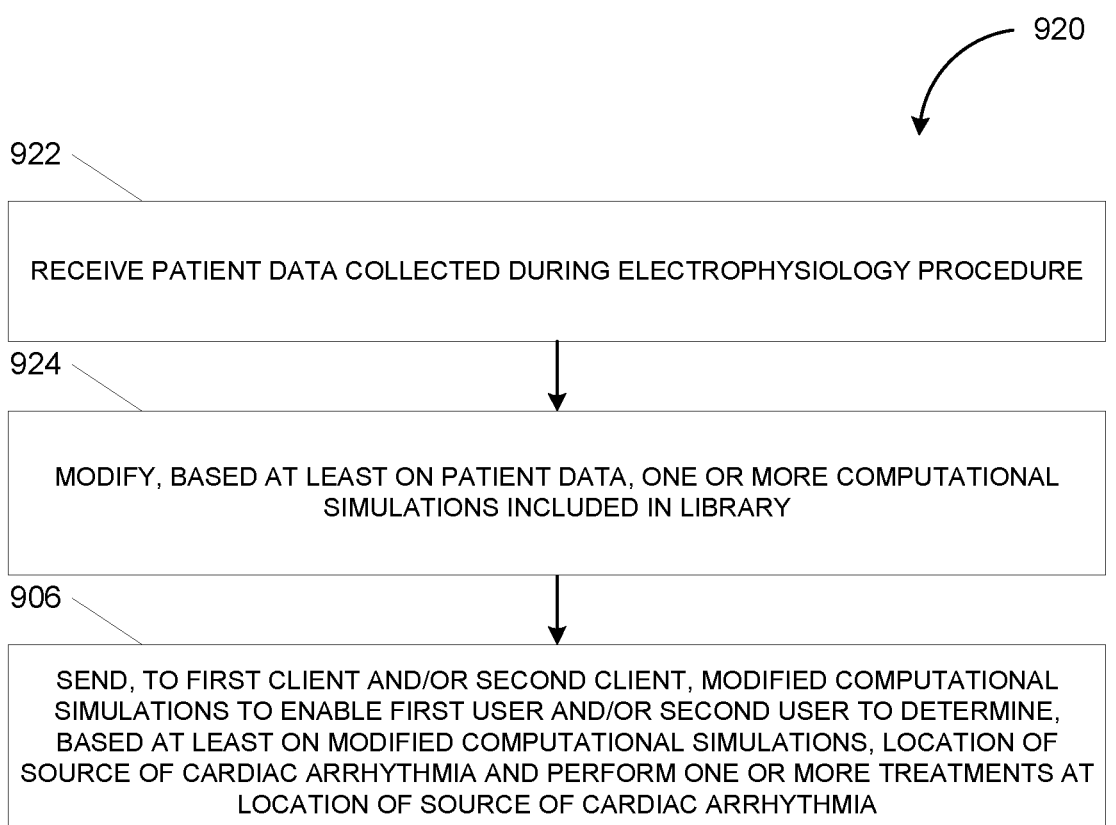

922

RECEIVE PATIENT DATA COLLECTED DURING ELECTROPHYSIOLOGY PROCEDURE

924

MODIFY, BASED AT LEAST ON PATIENT DATA, ONE OR MORE COMPUTATIONAL SIMULATIONS INCLUDED IN LIBRARY

906

SEND, TO FIRST CLIENT AND/OR SECOND CLIENT, MODIFIED COMPUTATIONAL SIMULATIONS TO ENABLE FIRST USER AND/OR SECOND USER TO DETERMINE, BASED AT LEAST ON MODIFIED COMPUTATIONAL SIMULATIONS, LOCATION OF SOURCE OF CARDIAC ARRHYTHMIA AND PERFORM ONE OR MORE TREATMENTS AT LOCATION OF SOURCE OF CARDIAC ARRHYTHMIA

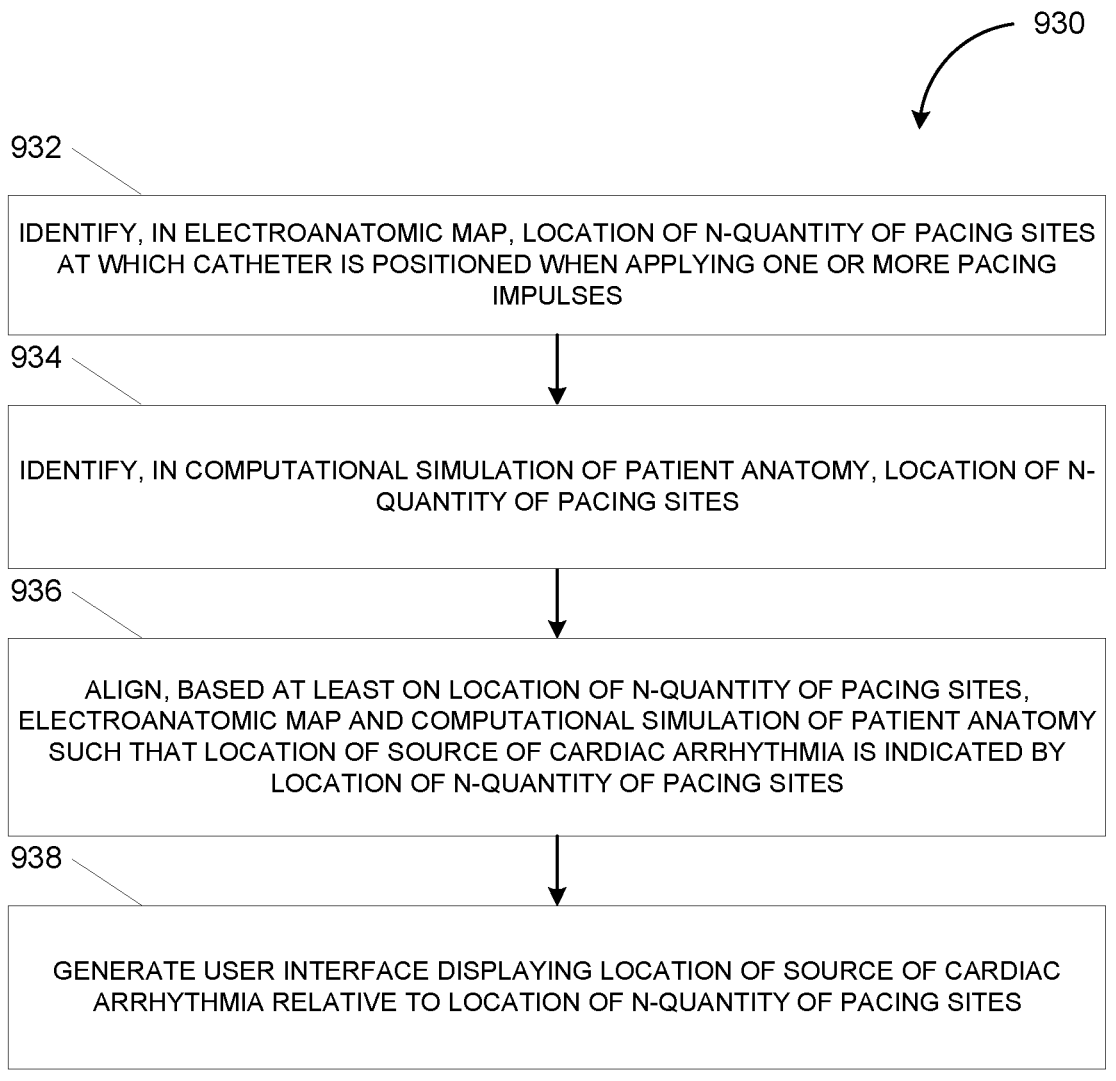

930

932

IDENTIFY, IN ELECTROANATOMIC MAP, LOCATION OF N-QUANTITY OF PACING SITES AT WHICH CATHETER IS POSITIONED WHEN APPLYING ONE OR MORE PACING IMPULSES

934

IDENTIFY, IN COMPUTATIONAL SIMULATION OF PATIENT ANATOMY, LOCATION OF N-QUANTITY OF PACING SITES

936

ALIGN, BASED AT LEAST ON LOCATION OF N-QUANTITY OF PACING SITES, ELECTROANATOMIC MAP AND COMPUTATIONAL SIMULATION OF PATIENT ANATOMY SUCH THAT LOCATION OF SOURCE OF CARDIAC ARRHYTHMIA IS INDICATED BY LOCATION OF N-QUANTITY OF PACING SITES

938

GENERATE USER INTERFACE DISPLAYING LOCATION OF SOURCE OF CARDIAC ARRHYTHMIA RELATIVE TO LOCATION OF N-QUANTITY OF PACING SITES

FIG. 9C

ENHANCED COMPUTATIONAL HEART SIMULATIONS

RELATED APPLICATION

This application is a national stage entry of Patent Cooperation Treaty Application No. PCT/US2019/069136 filed Dec. 31, 2019, entitled "ENHANCED COMPUTATIONAL HEART SIMULATIONS," which claims priority to U.S. Provisional Application No. 62/786,973 filed on Dec. 31, 2018, entitled "HEART RELATED SYSTEMS AND METHODS." The disclosures of which are incorporated herein by reference in their entirety. This application also incorporates by reference U.S. Pat. No. 10,319,144 "Computational Localization of Fibrillation Sources" regarding the computational model and the computational simulation library.

TECHNICAL FIELD

The subject matter described herein relates generally to computational modeling and simulations, and more specifically to enhancing computational modeling and simulations for identifying the locations of the sources of cardiac arrhythmias to enable targeted therapy.

BACKGROUND

Cardiac arrhythmias are common medical disorders in which abnormal electrical signals in the heart cause the heart to contract in a suboptimal manner. The resulting abnormal heartbeat, or arrhythmia, can occur in the atria of the heart (e.g., atrial fibrillation (AF)) and/or the ventricles of the heart (e.g., ventricular tachycardia (VT) or ventricular fibrillation (VF)). Treatments for cardiac arrhythmias attempt to address the mechanisms driving sustained and/or clinically significant episodes including, for example, stable electrical rotors, recurring electrical focal sources, reentrant electrical circuits, and/or the like. Left untreated, cardiac arrhythmias may cause serious complications including morbidity (e.g., syncope, stroke, and/or the like) and mortality (e.g. sudden cardiac death (SCD)).

SUMMARY

Systems, methods, and articles of manufacture, including computer program products, are provided for enhanced computational heart simulations. In some example embodiments, there is provided a system that includes at least one processor and at least one memory. The at least one memory may include program code that provides operations when executed by the at least one processor. The operations may include: receiving, from a first user, clinical data associated with a clinical case; indexing, based at least on a first plurality of characteristics associated with the clinical data, the clinical case, the indexing includes associating at least a portion of the clinical data with a computational simulation of cardiac arrhythmia having a second plurality of characteristics matching the first plurality of characteristics; and responding to a query from a second user by at least sending, to the second user, at least a portion of the clinical data associated with the indexed clinical case.

In some variations, one or more features disclosed herein including the following features can optionally be included in any feasible combination. The clinical data may include patient anatomic information, diagnostic and/or treatment modalities, treatment parameters, treatment outcome, and medical literature.

In some variations, the first plurality of characteristics and the second plurality of characteristics may include patient demographics, medical history, and treatment plan.

In some variations, the indexing may include determining, for each of a plurality of computational simulations of cardiac arrhythmias included in a library, a similarity score indicative of a closeness of match between the first plurality of characteristics associated with the clinical data and the second plurality of characteristics associated with each of the plurality of computational models and/or simulations. The indexing may further include associating at least the portion of the data with one of the plurality of computational models and/or simulations having a highest similarity score.

In some variations, at least the portion of the clinical data including the association with the computational simulation of cardiac arrhythmia may be stored at a data store.

In some variations, the query may include a vectorcardiogram (VCG) of a patient. The responding to query may include identifying the computational model of cardiac arrhythmia as most closely matching the vectorcardiogram of the patient and retrieving at least the portion of the clinical data associated with the indexed clinical case in order to send, to the second user, at least the portion of the clinical data.

In another aspect, there is provided a method for enhanced computational heart simulations. The method may include: receiving, from a first user, clinical data associated with a clinical case; indexing, based at least on a first plurality of characteristics associated with the clinical data, the clinical case, the indexing includes associating at least a portion of the clinical data with a computational simulation of cardiac arrhythmia having a second plurality of characteristics matching the first plurality of characteristics; and responding to a query from a second user by at least sending, to the second user, at least a portion of the clinical data associated with the indexed clinical case.

In some variations, one or more features disclosed herein including the following features can optionally be included in any feasible combination. The clinical data may include patient anatomic information, diagnostic and/or treatment modalities, treatment parameters, treatment outcome, and medical literature.

In some variations, the first plurality of characteristics and the second plurality of characteristics may include patient demographics, medical history, and treatment plan.

In some variations, the indexing may include determining, for each of a plurality of computational simulations of cardiac arrhythmias included in a library, a similarity score indicative of a closeness of match between the first plurality of characteristics associated with the clinical data and the second plurality of characteristics associated with each of the plurality of computational simulations. The indexing may further include associating at least the portion of the data with one of the plurality of computational simulations having a highest similarity score.

In some variations, the method may further include storing, at a data store, at least the portion of the clinical data including the association with the computational simulation of cardiac arrhythmia.

In some variations, the query may include a vectorcardiogram (VCG) of a patient. The responding to query may include identifying the computational model of cardiac arrhythmia as most closely matching the vectorcardiogram of the patient and retrieving at least the portion of the clinical data associated with the indexed clinical case in order to send, to the second user, at least the portion of the clinical data.

In another aspect, there is provided a computer program product including a non-transitory computer readable medium storing instructions. The instructions may cause operations may executed by at least one data processor. The operations may include: receiving, from a first user, clinical data associated with a clinical case; indexing, based at least on a first plurality of characteristics associated with the clinical data, the clinical case, the indexing includes associating at least a portion of the clinical data with a computational simulation of cardiac arrhythmia having a second plurality of characteristics matching the first plurality of characteristics; and responding to a query from a second user by at least sending, to the second user, at least a portion of the clinical data associated with the indexed clinical case.

In another aspect, there is provide an apparatus for enhanced computational heart simulations. The apparatus may include: means for receiving, from a first user, clinical data associated with a clinical case; means for indexing, based at least on a first plurality of characteristics associated with the clinical data, the clinical case, the indexing includes associating at least a portion of the clinical data with a computational model and simulation of cardiac arrhythmia having a second plurality of characteristics matching the first plurality of characteristics; and means for responding to a query from a second user by at least sending, to the second user, at least a portion of the clinical data associated with the indexed clinical case.

In another aspect, there is provided a system that includes at least one processor and at least one memory. The at least one memory may include program code that provides operations when executed by the at least one processor. The operations may include: receiving patient data collected during an electrophysiology procedure; modifying, based at least on the patient data, one or more computational models and/or simulations of cardiac arrhythmia; determining, based at least on the modified one or more computational models and/or simulations of cardiac arrhythmia, a location of a source of the cardiac arrhythmia; and providing an indication of the location of the source of the cardiac arrhythmia to inform treatment based on the patient data.

In some variations, one or more features disclosed herein including the following features can optionally be included in any feasible combination. The patient data may include at least one of an action potential duration restitution data, conduction velocity restitution data, patient anatomical geometry, voltage mapping, intracardiac ultrasound data, transthoracic ultrasound data, cone-beam computed tomography data, fluoroscopy data, patient demographics, cardiac activation pattern, regional conduction velocity, and electrogram characteristics.

In some variations, the modifying may include applying, to the one or more computational models and/or simulations, a patient-specific enhancement including at least one of a geometrical morphing and/or rotating, imposing a voltage and/or electrogram information onto the one or more computational simulations, indicating an activation information, adding global and/or regional information regarding a thickness of cardiac structure walls, and incorporating global and/or geographical information regarding the position and morphology of papillary muscles, pulmonary veins, and/or left and right atrial appendages.

In some variations, the modifying may be performed in real time or near real time. The modified one or more computational simulations of cardiac arrhythmia may be returned to a user for clinical use.

In some variations, the one or more computational models and/or simulations may be part of a library of non-patient specific computational simulations of cardiac arrhythmia.

In some variations, an arrhythmia simulation may be initiated based at least on one or more arrhythmia solutions associated with the modified one or more computational simulations of cardiac arrhythmia to generate a patient-tailored arrhythmia vectorcardiogram library for use in a computational arrhythmia mapping process.

In some variations, an arrhythmia simulation may be performed for each of a plurality of source locations based at least on the modified one or more computational simulations of cardiac arrhythmia. The arrhythmia simulation may be performed based on an assumption of the source location. The plurality of source locations and the corresponding arrhythmia simulations may form a patient-tailored arrhythmia library for use in a computational arrhythmia mapping process.

In another aspect, there is provided a method for enhanced computational heart simulations. The method may include: receiving patient data collected during an electrophysiology procedure; modifying, based at least on the patient data, one or more computational models and/or simulations of cardiac arrhythmia; determining, based at least on the modified one or more computational models and/or simulations of cardiac arrhythmia, a location of a source of the cardiac arrhythmia; and providing an indication of the location of the source of the cardiac arrhythmia to inform treatment based on the patient data.

In some variations, one or more features disclosed herein including the following features can optionally be included in any feasible combination. The patient data may include at least one of an action potential duration restitution data, conduction velocity restitution data, patient anatomical geometry, voltage mapping, intracardiac ultrasound data, transthoracic ultrasound data, cone-beam computed tomography data, fluoroscopy data, patient demographics, cardiac activation pattern, regional conduction velocity, and electrogram characteristics.

In some variations, the modifying may include applying, to the one or more computational models and/or simulations, a patient-specific enhancement including at least one of a geometrical morphing and/or rotating, imposing a voltage and/or electrogram information onto the one or more computational simulations, indicating an activation information, adding global and/or regional information regarding a thickness of cardiac structure walls, and incorporating global and/or geographical information regarding the position and morphology of papillary muscles, pulmonary veins, and/or left and right atrial appendages.

In some variations, the modifying may be performed in real time or near real time. The modified one or more computational simulations of cardiac arrhythmia may be returned to a user for clinical use.

In some variations, the one or more computational models and/or simulations may be part of a library of non-patient specific computational simulations of cardiac arrhythmia.

In some variations, the method may further include initiating, based at least on one or more arrhythmia solutions associated with the modified one or more computational simulations of cardiac arrhythmia, an arrhythmia simulation to generate a patient-tailored arrhythmia vectorcardiogram library for use in a computational arrhythmia mapping process.

In some variations, the method may further include performing, for each of a plurality of source locations, an arrhythmia simulation based at least on the modified one or more computational simulations of cardiac arrhythmia. The arrhythmia simulation may be performed based on an assumption of the source location. The plurality of source locations and the corresponding arrhythmia simulations may form a patient-tailored arrhythmia library for use in a computational arrhythmia mapping process.

In another aspect, there is provided a computer program product including a non-transitory computer readable medium storing instructions. The instructions may cause operations which may be executed by at least one data processor. The operations may include: receiving patient data collected during an electrophysiology procedure; modifying, based at least on the patient data, one or more computational simulations of cardiac arrhythmia; determining, based at least on the modified one or more computational simulations of cardiac arrhythmia, a location of a source of the cardiac arrhythmia; and providing an indication of the location of the source of the cardiac arrhythmia to inform treatment based on the patient data.

In another aspect, there is provided an apparatus for enhanced computational heart simulations. The apparatus may include: means for receiving patient data collected during an electrophysiology procedure; means for modifying, based at least on the patient data, one or more computational simulations of cardiac arrhythmia; means for determining, based at least on the modified one or more computational models and simulations of cardiac arrhythmia, a location of a source of the cardiac arrhythmia; and means for providing an indication of the location of the source of the cardiac arrhythmia to inform treatment based on the patient data.

In another aspect, there is provided a system that includes at least one processor and at least one memory. The at least one memory may include program code that provides operations when executed by the at least one processor. The operations may include: determining, in an electroanatomic map, a location of each of an n-quantity of pacing sites at which a catheter, a pacemaker lead, or an implantable cardioverter defibrillator lead is positioned when applying one or more pacing impulses; identifying, for each of the n-quantity of pacing sites, a computational model and arrhythmia simulation associated with a vectorcardiogram that matches a patient vectorcardiogram collected while pacing at each of the n-quantity of pacing sites and selecting one or more corresponding pacing sites in the computational model; aligning, based at least on the t location of each of the n-quantity of pacing sites in the electroanatomic map and the computational model, the electroanatomic map and the computational model; and generating, based at least on the aligning, an indication of a location of a source of a clinically relevant cardiac arrhythmia in the computational model relative to the location of each of the n-quantity of pacing sites.

In some variations, one or more features disclosed herein including the following features can optionally be included in any feasible combination. The n-quantity of pacing sites may include at least three pacing sites.

In some variations, the aligning may include applying a transformative matrix to align a first reference coordinate system of the electroanatomic map and a second reference coordinate system of the computational simulation.

In some variations, the location of the source of the clinically relevant cardiac arrhythmia may be further translated into an electroanatomic mapping system based at least on a prolate spheroidal coordinate system.

In some variations, a treatment may be applied, based at least on the indication, to the location of the source of the clinically relevant cardiac arrhythmia. The treatment may include at least one of an ablation, targeted gene therapy, radiation therapy, and surgical intervention.

In some variations, the computational model, the electroanatomic map, and a mapping result with the n-quantity pacing sites aligned may be displayed.

In another aspect, there is provided a method for enhanced computational heart simulations. The method may include: determining, in an electroanatomic map, a location of each of an n-quantity of pacing sites at which a catheter, a pacemaker lead, or an implantable cardioverter defibrillator lead is positioned when applying one or more pacing impulses; identifying, for each of the n-quantity of pacing sites, a computational model and arrhythmia simulation associated with a vectorcardiogram that matches a patient vectorcardiogram collected while pacing at each of the n-quantity of pacing sites and selecting one or more corresponding pacing sites in the computational model; aligning, based at least on the location of each of the n-quantity of pacing sites in the electroanatomic map and the computational model, the electroanatomic map and the computational model; and generating, based at least on the aligning, an indication of a location of a source of a clinically relevant cardiac arrhythmia in the computational model relative to the location of each of the n-quantity of pacing sites.

In some variations, one or more features disclosed herein including the following features can optionally be included in any feasible combination. The n-quantity of pacing sites may include at least three pacing sites.

In some variations, the aligning may include applying a transformative matrix to align a first reference coordinate system of the electroanatomic map and a second reference coordinate system of the computational simulation.

In some variations, the location of the source of the clinically relevant cardiac arrhythmia may be further translated into an electroanatomic mapping system based at least on a prolate spheroidal coordinate system.

In some variations, a treatment may be applied, based at least on the indication, to the location of the source of the clinically relevant cardiac arrhythmia. The treatment may include at least one of an ablation, targeted gene therapy, radiation therapy, and surgical intervention.

In some variations, the method may further include displaying the computational model, the electroanatomic map, and a mapping result with the n-quantity pacing sites aligned.

In another aspect, there is provided a computer program product including a non-transitory computer readable medium storing instructions. The instructions may cause operations may executed by at least one data processor. The operations may include: determining, in an electroanatomic map, a location of each of an n-quantity of pacing sites at which a catheter, a pacemaker lead, or an implantable cardioverter defibrillator lead is positioned when applying one or more pacing impulses; identifying, for each of the n-quantity of pacing sites, a computational model and arrhythmia simulation associated with a vectorcardiogram that matches a patient vectorcardiogram collected while pacing at each of the n-quantity of pacing sites and selecting one or more corresponding pacing sites in the computational model; aligning, based at least on the location of each of the n-quantity of pacing sites in the electroanatomic map and the computational model, the electroanatomic map and the computational model; and generating, based at least on the aligning, an indication of a location of a source of a clinically relevant cardiac arrhythmia in the computational model relative to the location of each of the n-quantity of pacing sites.

In another aspect, there is provided an apparatus for enhanced computational heart simulations. The apparatus may include: means for determining, in an electroanatomic map, a location of each of an n-quantity of pacing sites at which a catheter, a pacemaker lead, or an implantable cardioverter defibrillator lead is positioned when applying one or more pacing impulses; means for identifying, for each of the n-quantity of pacing sites, a computational model and/or arrhythmia simulation associated with a vectorcardiogram that matches a patient vectorcardiogram collected while pacing at each of the n-quantity of pacing sites and selecting one or more corresponding pacing sites in the computational model; means for aligning, based at least on the t location of each of the n-quantity of pacing sites in the electroanatomic map and the computational model, the electroanatomic map and the computational model; and means for generating, based at least on the aligning, an indication of a location of a source of a clinically relevant cardiac arrhythmia in the computational model relative to the location of each of the n-quantity of pacing sites.

Implementations of the current subject matter can include systems and methods consistent including one or more features are described as well as articles that comprise a tangibly embodied machine-readable medium operable to cause one or more machines (e.g., computers, etc.) to result in operations described herein. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connection including, for example, a connection over a network (e.g. the Internet, a wireless wide area network, a local area network, a wide area network, a wired network, or the like), a direct connection between one or more of the multiple computing systems, and/or the like.

The details of one or more variations of the subject matter described herein are set forth in the accompanying drawings and the description below. Other features and advantages of the subject matter described herein may be apparent from the description and drawings, and from the claims. While certain features of the currently disclosed subject matter are described for illustrative purposes in relation to computational heart simulations, it should be readily understood that such features are not intended to be limiting. The claims that follow this disclosure are intended to define the scope of the protected subject matter.

DESCRIPTION OF THE DRAWINGS

The accompanying drawings, which are incorporated in and constitute a part of this specification, show certain aspects of the subject matter disclosed herein and, together

Figure 1:
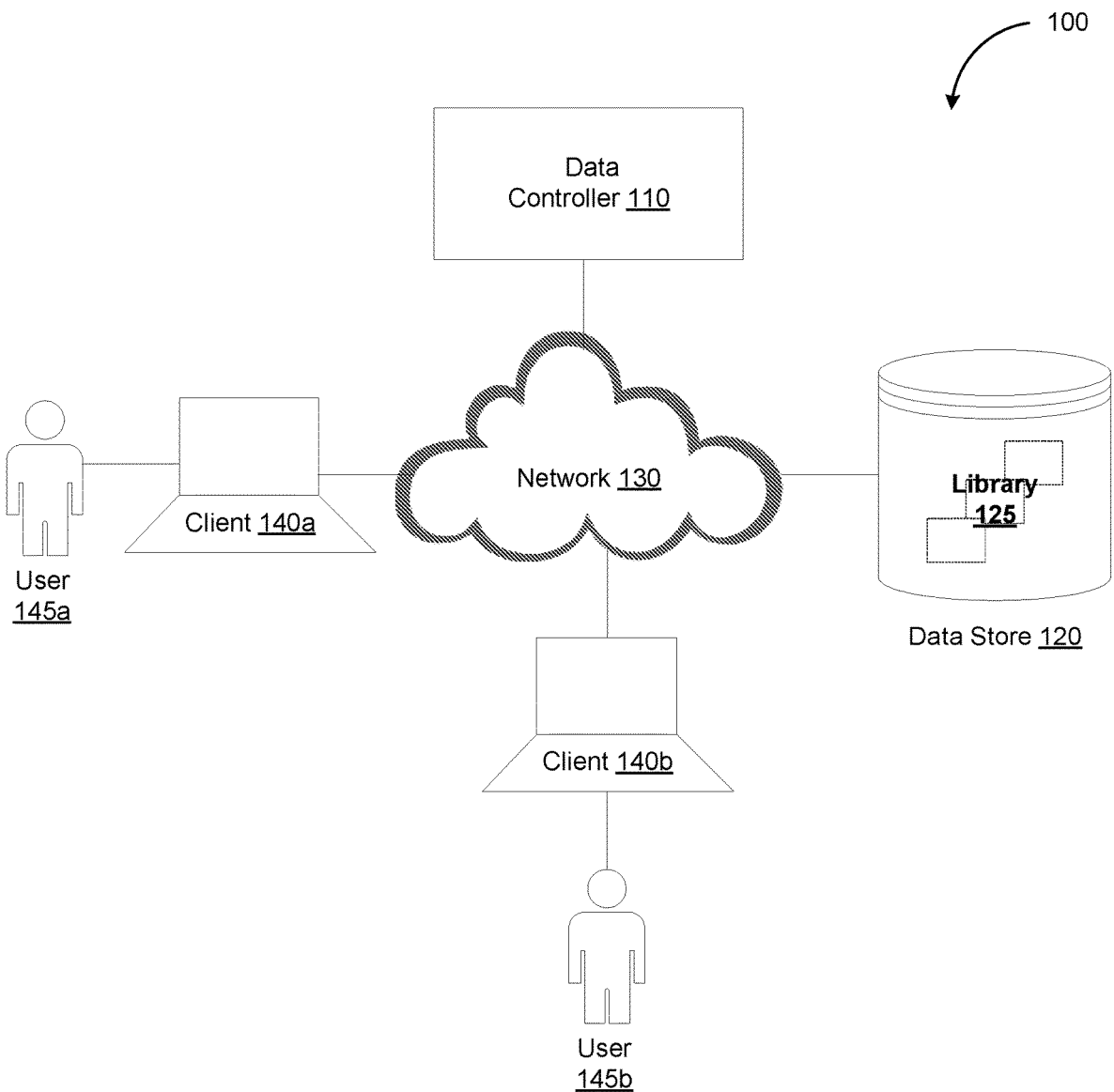
Figure 2:
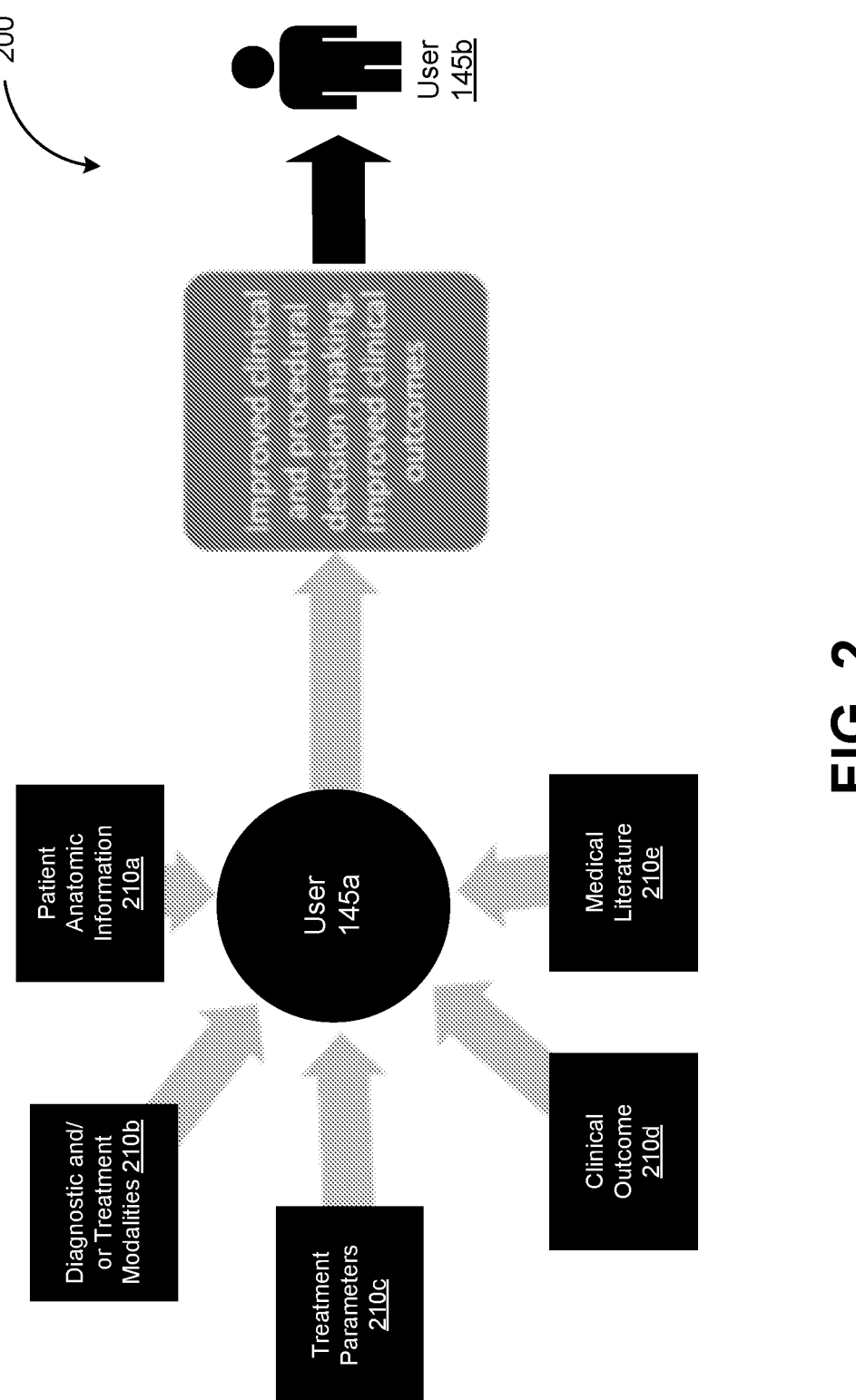
Figure 3A:
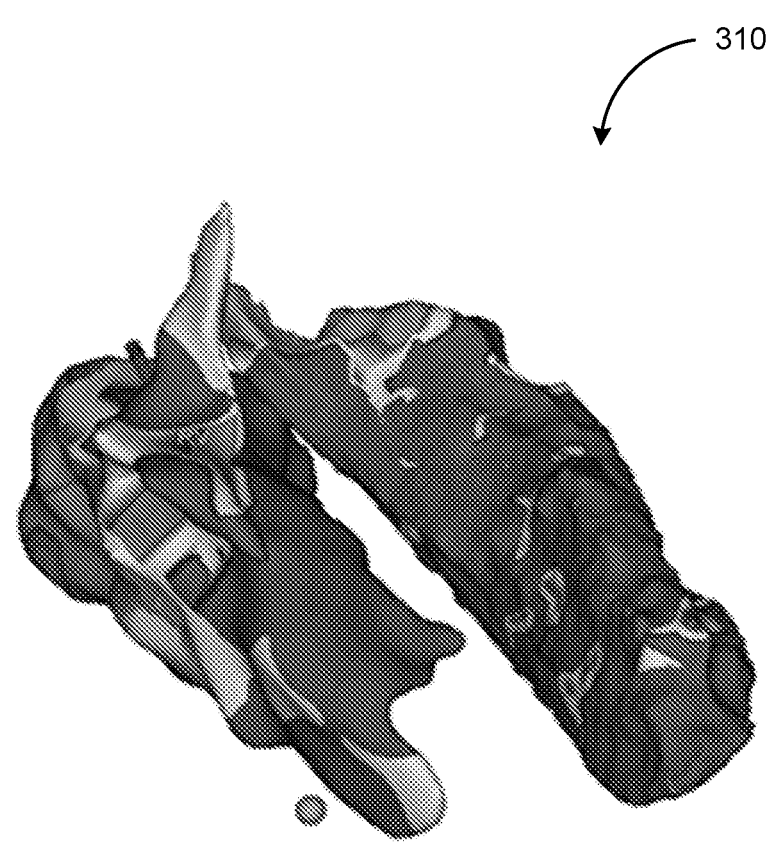
Figure 3B:
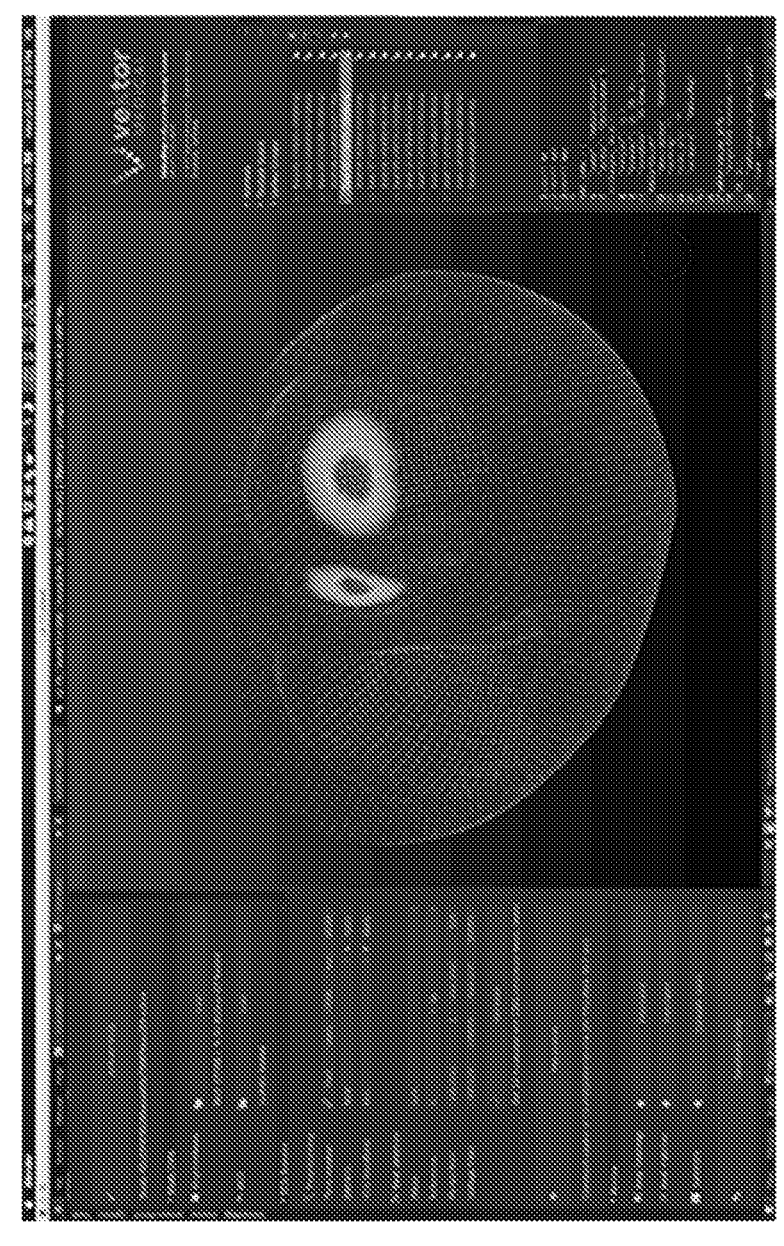
Figure 3C:
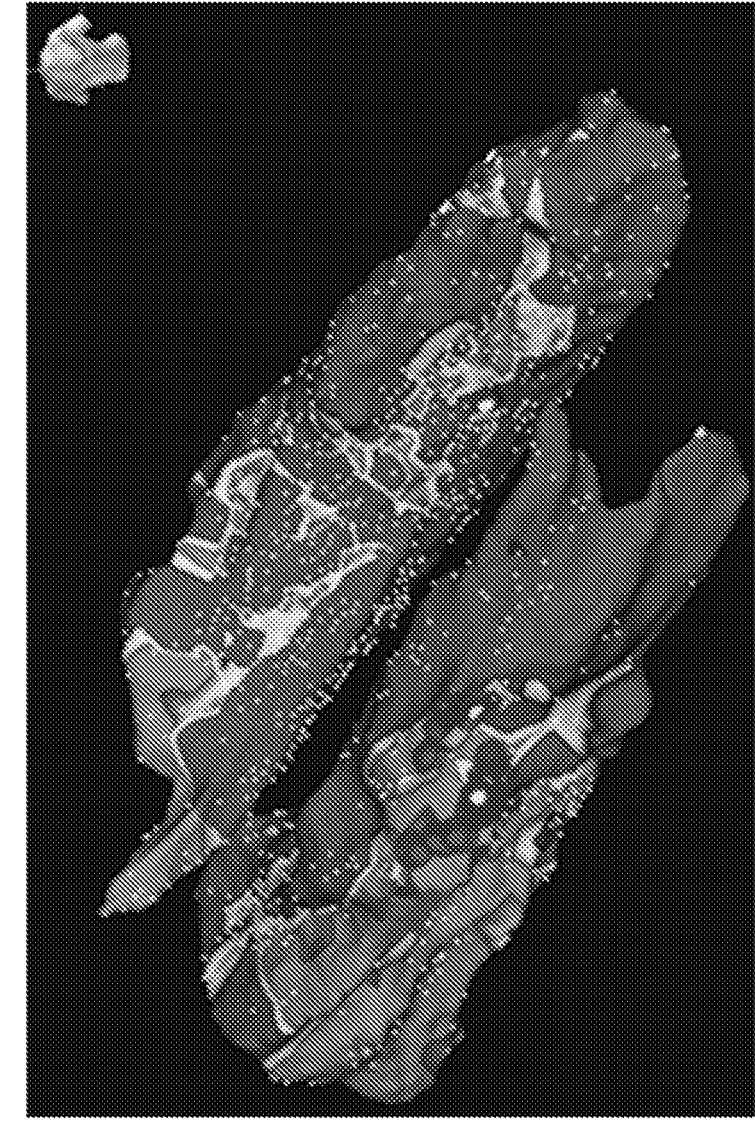
Figure 3D:
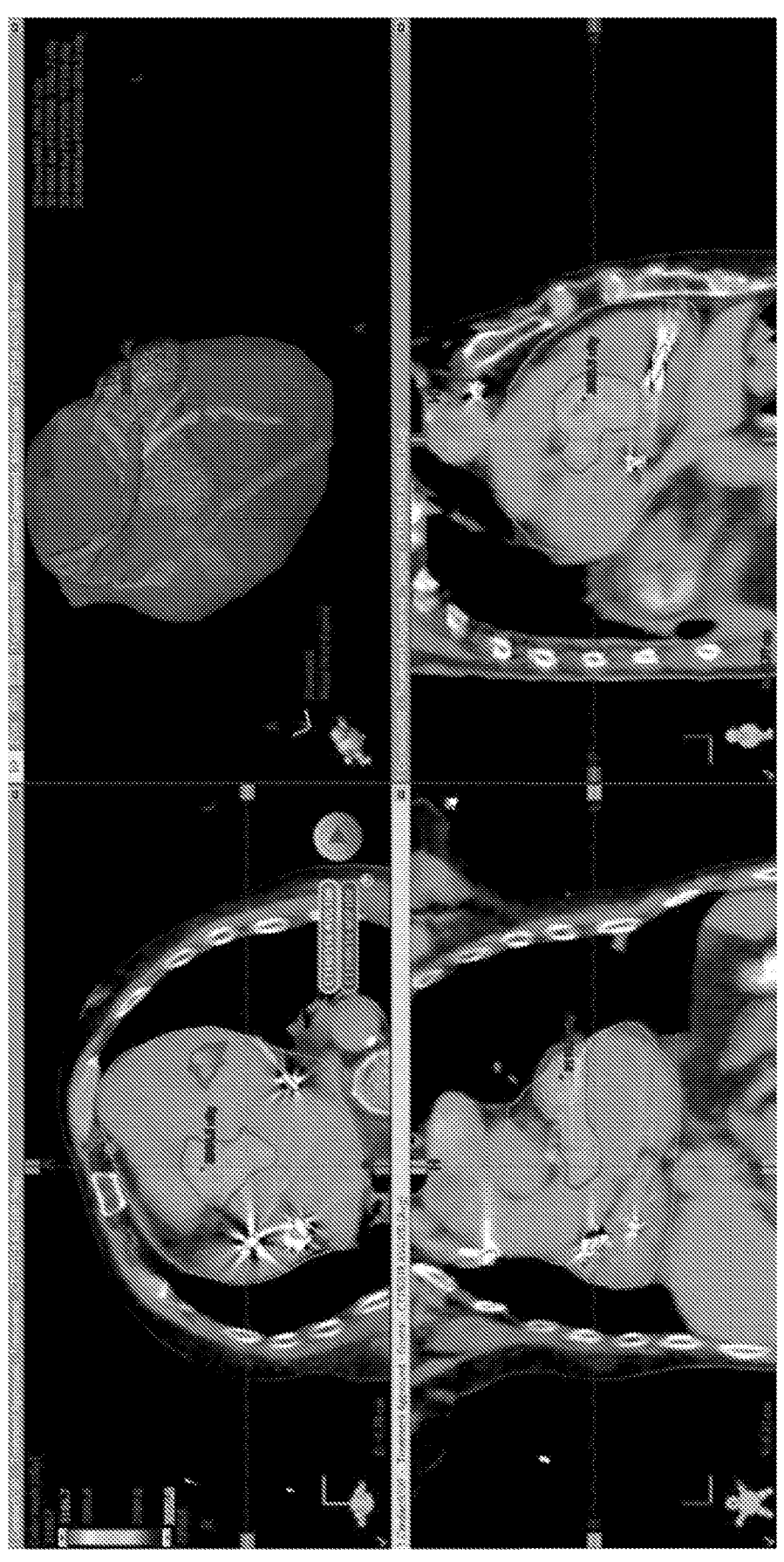
Figure 4:
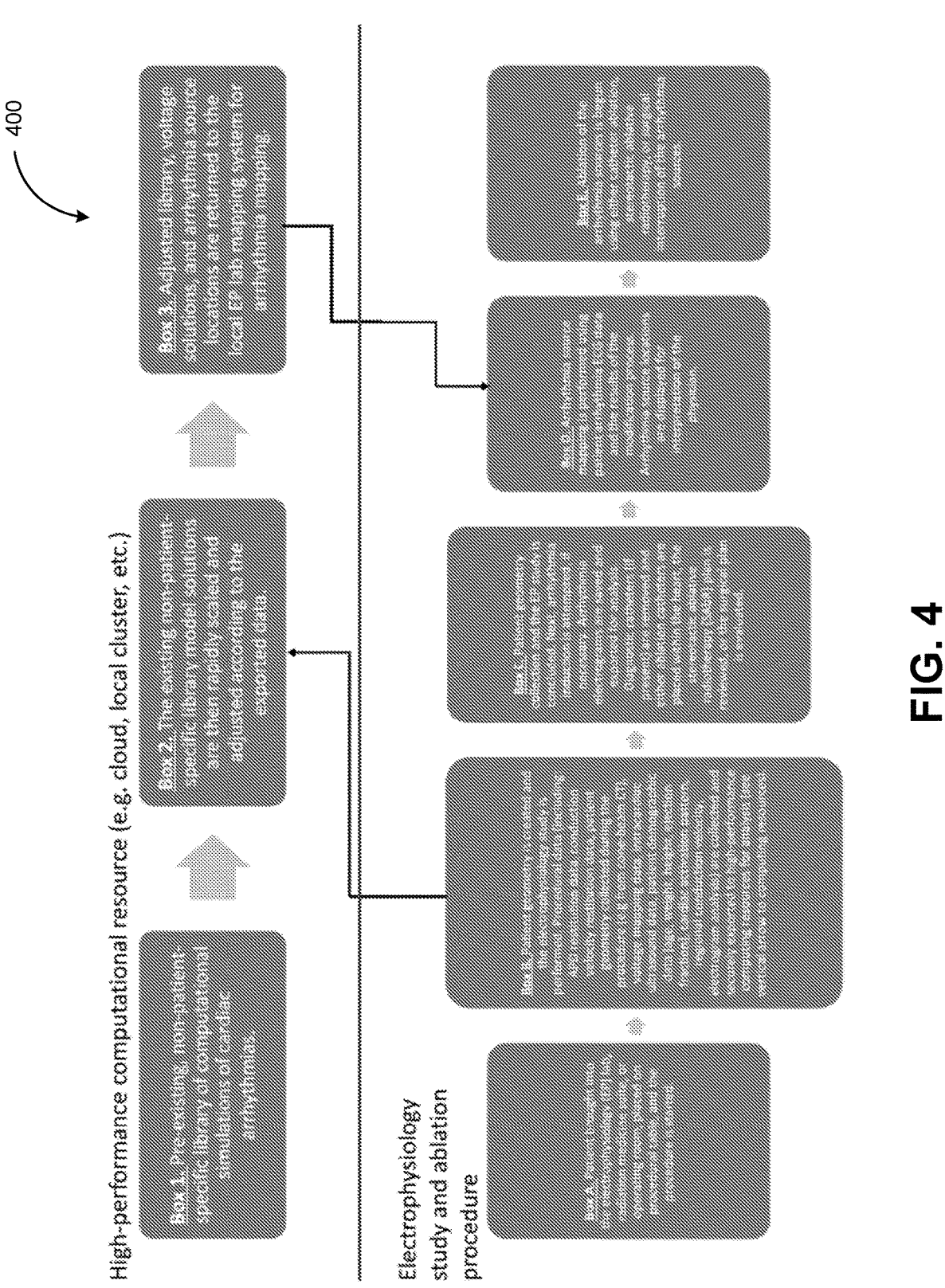
Figure 5A:
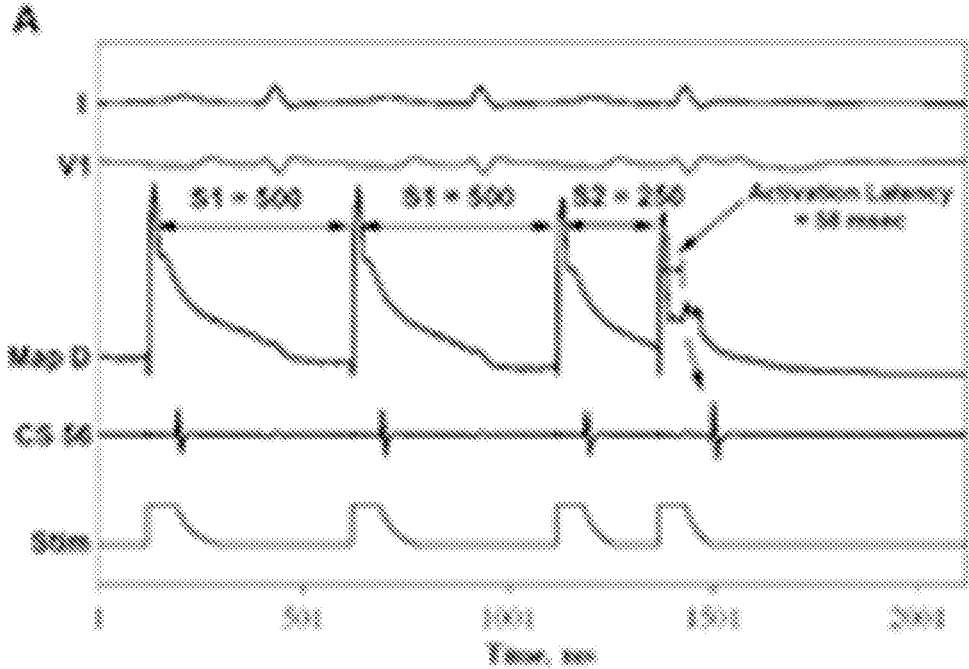
Figure 5B:
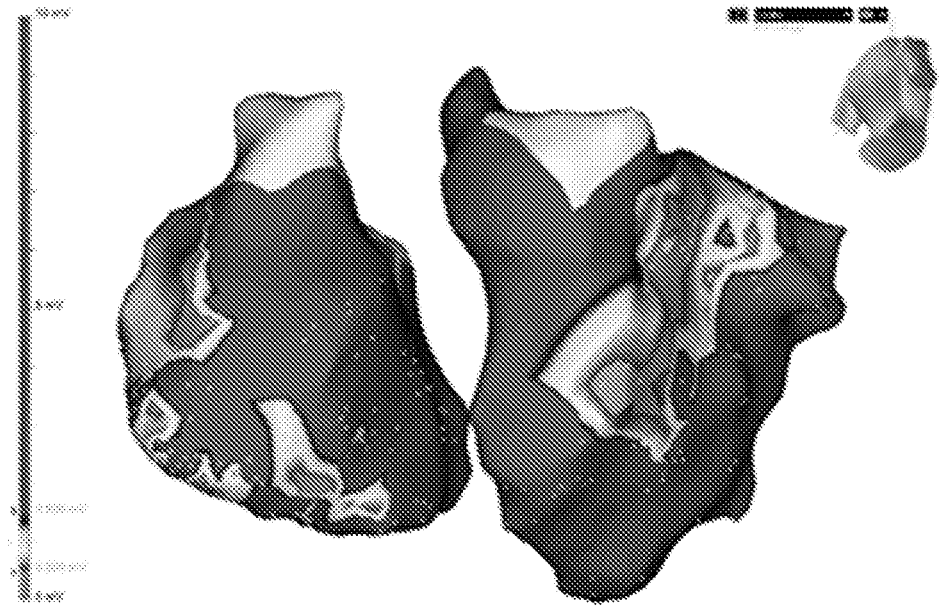
Figure 5C:
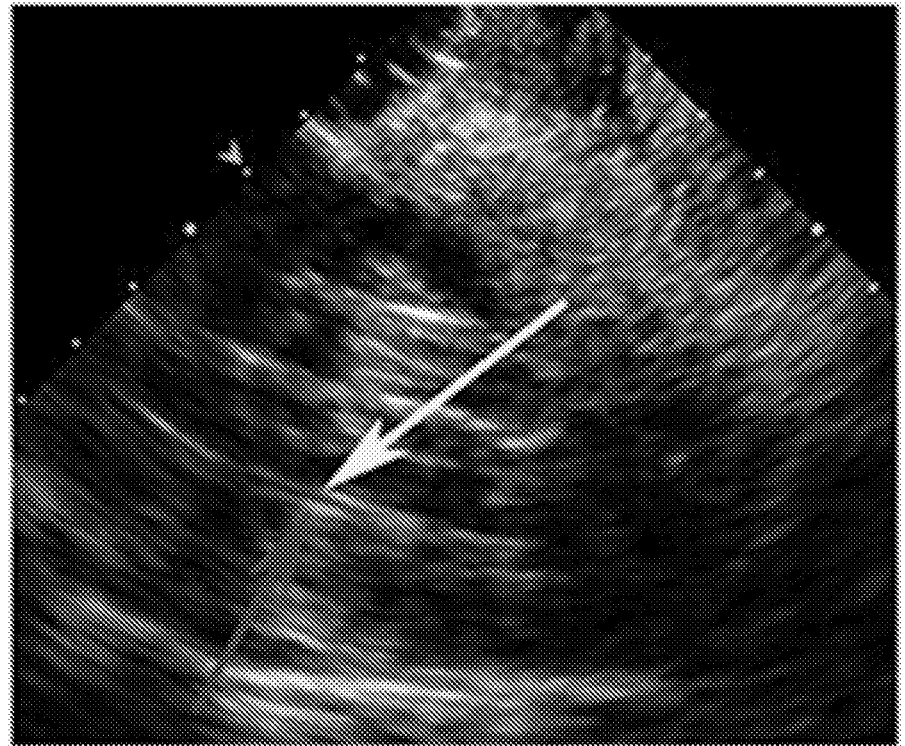
Figure 6A:
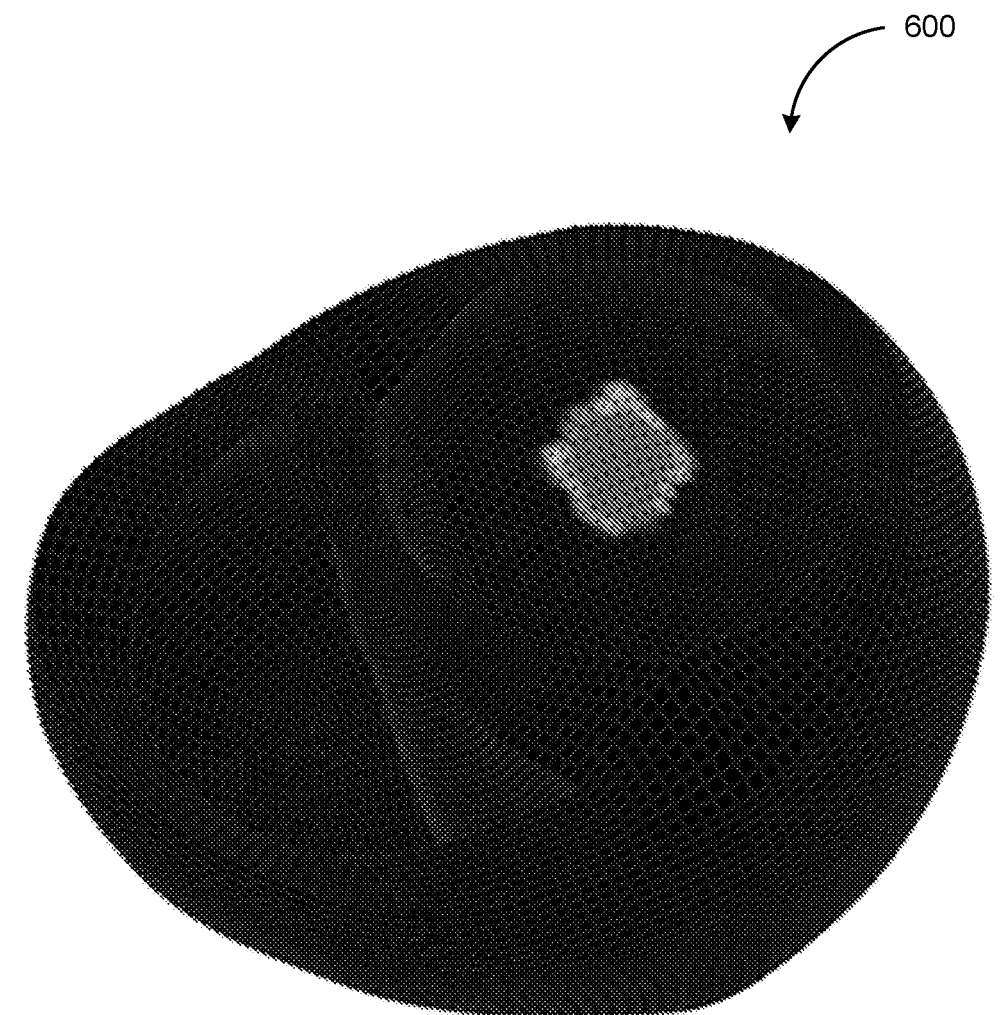
Figure 6B:
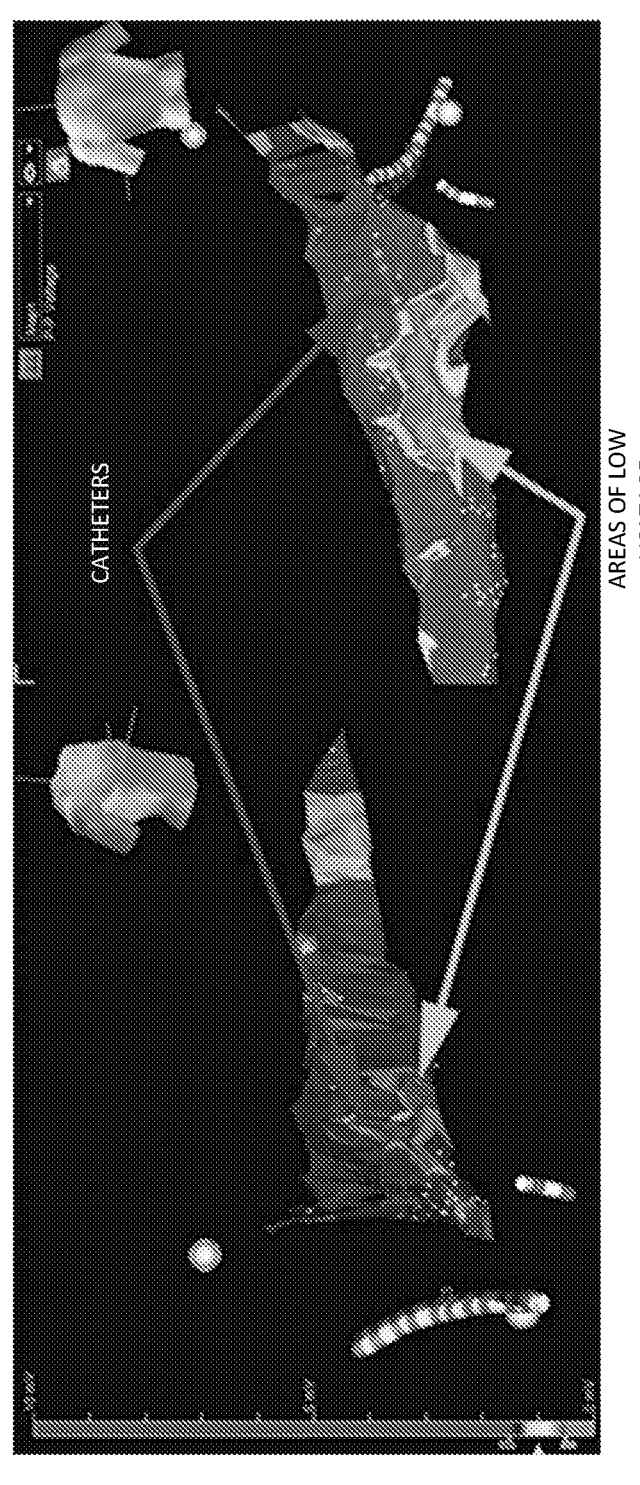
Figure 6C:
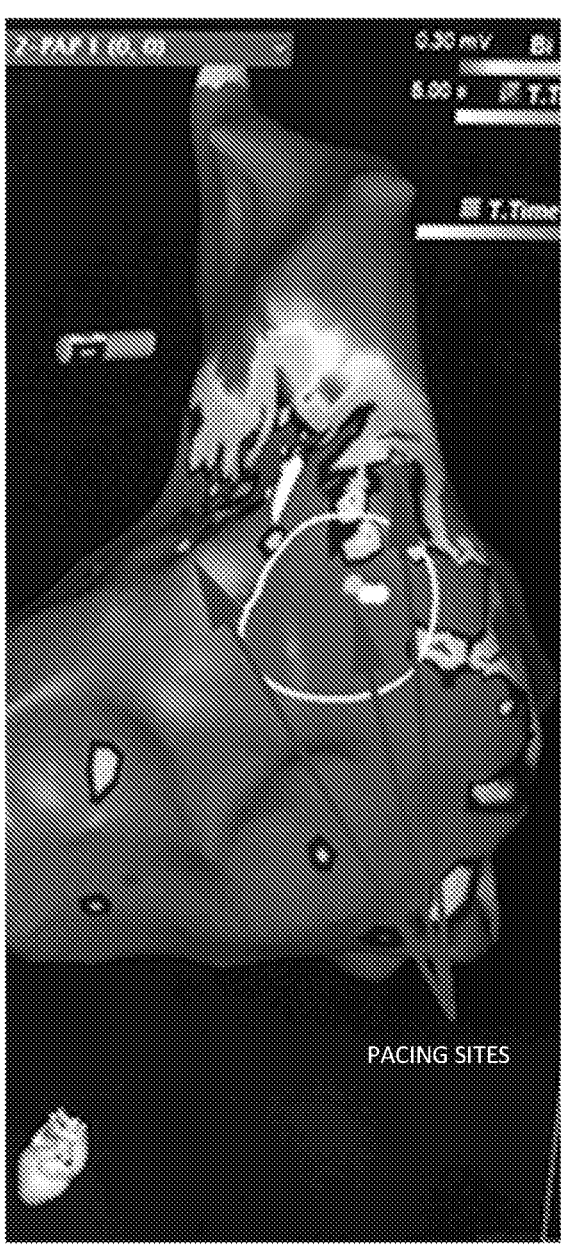
Figure 6D:
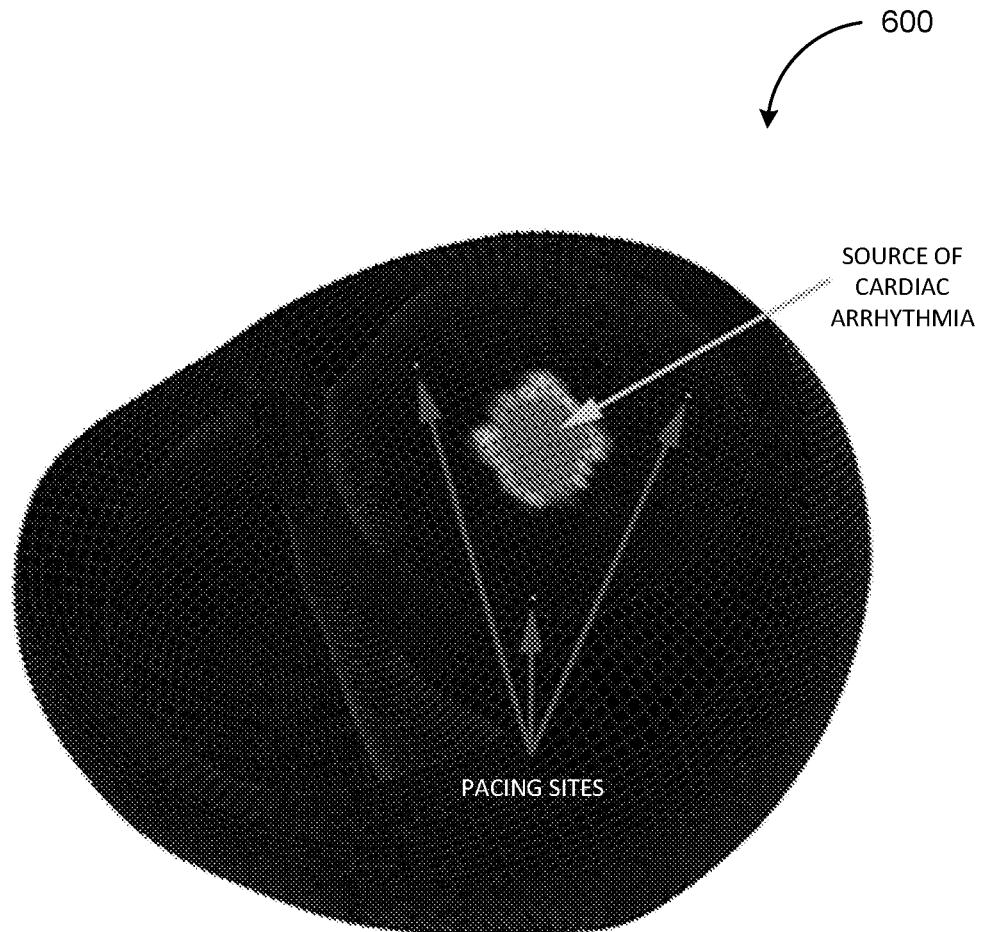
Figure 7A:
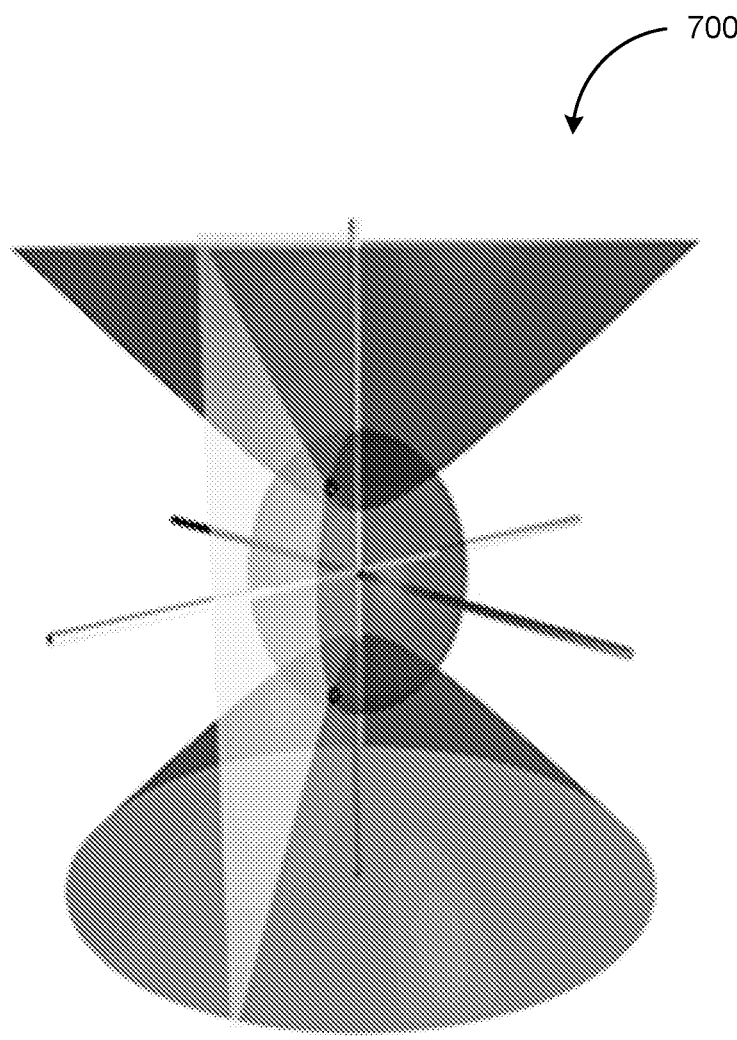
Figure 7B:
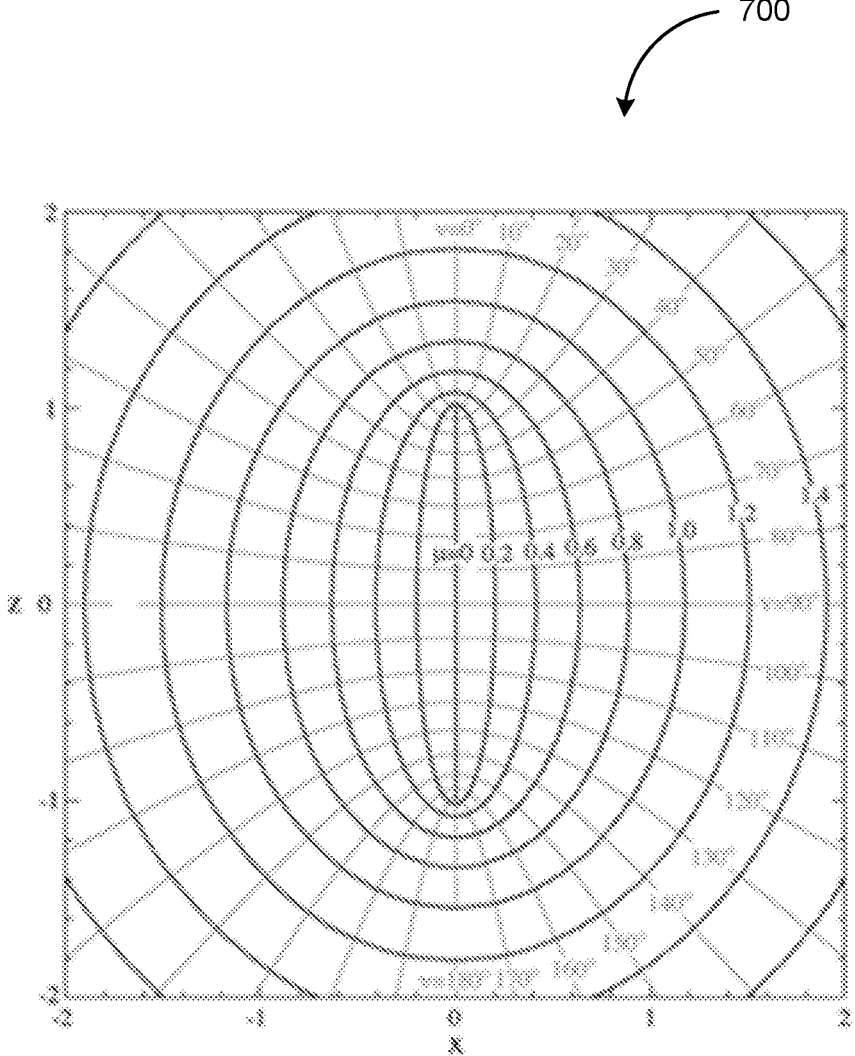
Figure 8A:
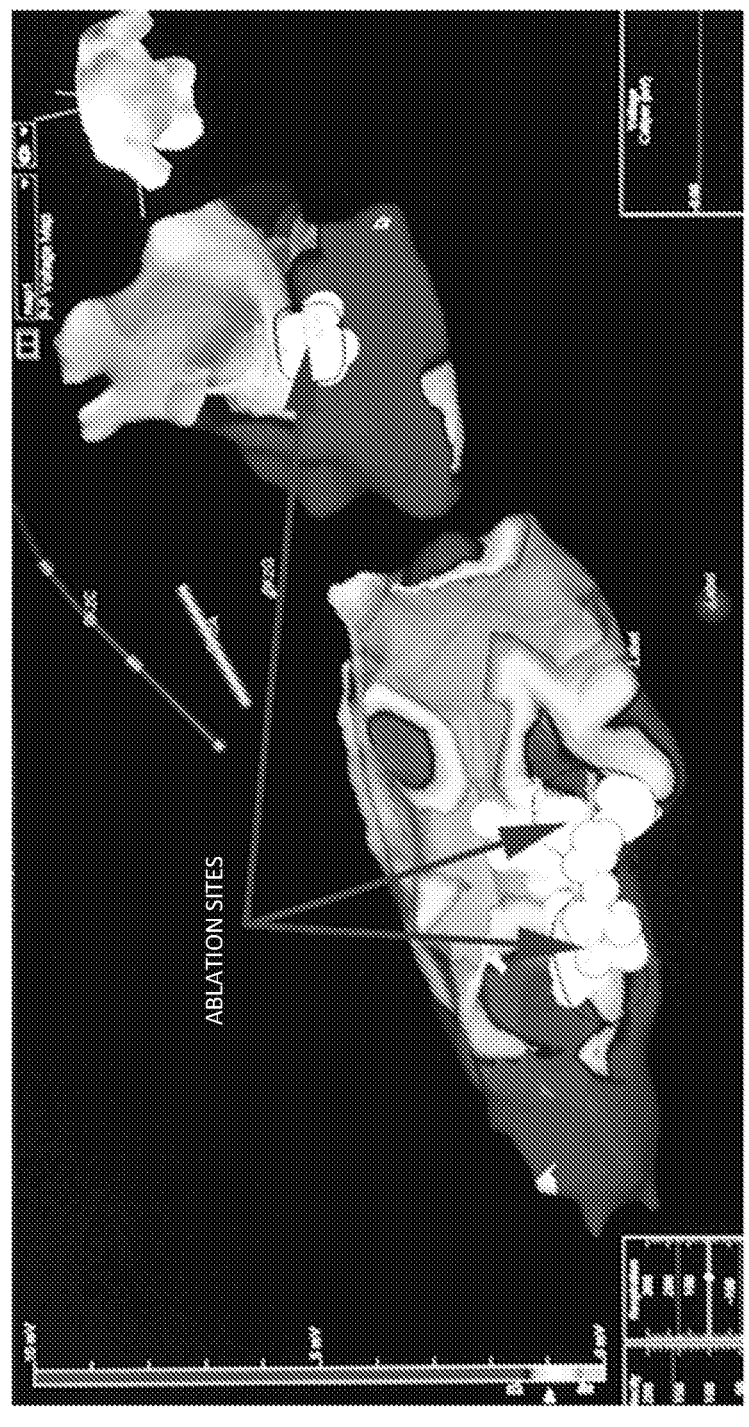
Figure 8B:
Figure 10:
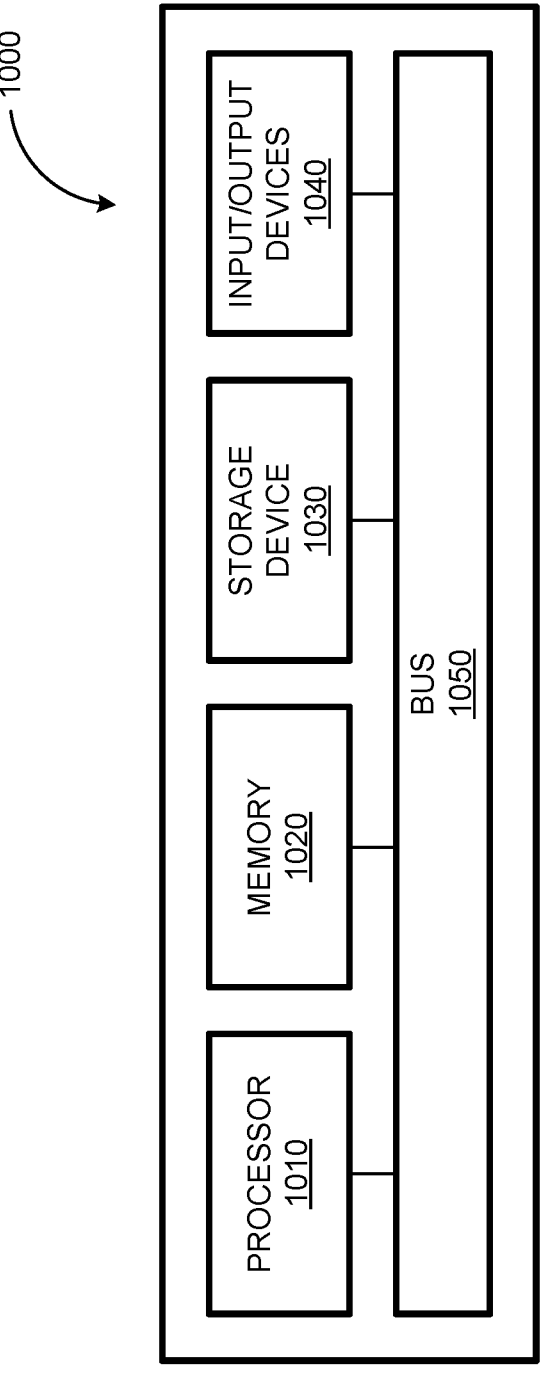

8 with the description, help explain some of the principles associated with the disclosed implementations. In the drawings, FIG. 1 depicts a system diagram illustrating an example of a cardiac arrhythmia control system, in accordance with some example embodiments;

FIG. 2 depicts a flow diagram illustrating an example of a data flow in a cardiac arrhythmia control system, in accordance with some example embodiments;

FIG. 3A depicts an example of data associated with a clinical case, in accordance with some example embodiments;

FIG. 3B depicts an example of a user interface, in accordance with some example embodiments;

FIG. 3C depicts another example of data associated with a clinical case, in accordance with some example embodiments;

FIG. 3D depicts another example of data associated with a clinical case, in accordance with some example embodiments;

FIG. 4 depicts a flowchart illustrating an example of a process for modifying a library of non-patient specific computational simulations, in accordance with some example embodiments;

FIG. 5A depicts an example of data collected during an electrophysiology procedure, in accordance with some example embodiments;

FIG. 5B depicts another example of data collected during an electrophysiology procedure, in accordance with some example embodiments;

FIG. 5C depicts another example of data collected during an electrophysiology procedure, in accordance with some example embodiments;

FIG. 6A depicts an example of a computational model of a cardiac arrhythmia, in accordance with some example embodiments;

FIG. 6B depicts an example of an electroanatomic mapping, in accordance with some example embodiments;

FIG. 6C depicts an example of an electroanatomic mapping including pacing sites, in accordance with some example embodiments;

FIG. 6D depicts an example of a computational model of a cardiac arrhythmia with the identified locations of pacing sites, in accordance with some example embodiments; and FIG. 7A depicts a geometry of a prolate spheroidal coordinate system, in accordance with some example embodiments;

FIG. 7B depicts a prolate spheroidal coordinate system, in accordance with some example embodiments;

FIG. 8A depicts an example of an electroanatomic mapping including a cardiac geometry and ablation sites, in accordance with some example embodiments;

FIG. 8B depicts an example of a stereotactic ablative radiotherapy case, in accordance with some example embodiments;

FIG. 9A depicts a flowchart illustrating an example of a process for enhancing a library of computational simulations with data associated with clinical cases, in accordance with some example embodiments;

FIG. 9B depicts a flowchart illustrating an example of a process for modifying a library of computational simulations, in accordance with some example embodiments;

FIG. 9C depicts a flowchart illustrating an example of a process for aligning a computational simulation with an electroanatomic mapping, in accordance with some example embodiments; and FIG. 10 depicts a block diagram illustrating a computing system, in accordance with some example embodiments.

When practical, similar reference numbers denote similar structures, features, or elements.

DETAILED DESCRIPTION

Cardiac arrhythmias (e.g., atrial fibrillation, ventricular tachycardia, ventricular fibrillation) may be treated by targeting the mechanisms driving sustained and/or clinically significant episodes including, for example, stable electrical rotors, recurring electrical focal sources, reentrant electrical circuits, and/or the like. Ablation is one example treatment for cardiac arrhythmias in which radiofrequency, cryogenic temperatures, ultrasound, and/or radiation (e.g. stereotactic ablative radiotherapy (SAbR)) may be applied to the source of the cardiac arrhythmia. The resulting lesions may alleviate cardiac arrhythmia by disrupting and/or eliminating the erratic electric signals causing the abnormal heart activation. Nevertheless, the outcome of ablation may depend on a variety of factors including a correct localization of the source of cardiac arrhythmia. With existing methodologies, correctly localizing the source of cardiac arrhythmia remains a challenge. Moreover, the absence of sufficient access to prior clinical case data, including relevant patient anatomy, treatment parameters, and treatment outcome, may be further disadvantage some practitioners treating patients for cardiac arrhythmias. As such, various implementations of the current subject matter include techniques for enhancing computational heart simulations to improve cardiac arrhythmia source localization to facilitate diagnosis and targeted treatment.

In some example embodiments, a library including a plurality of computational models and/or simulations of cardiac arrhythmias (described in U.S. Pat. No. 10,319,144 "Computational Localization of Fibrillation Sources") may be enhanced with clinical data associated with clinical cases. For example, a first user may send, to a data controller associated with the library, clinical data associated with a clinical case that includes patient anatomic information, data such as voltage maps or electrogram characteristics, diagnostic and/or treatment modalities, treatment parameters, treatment outcome, relevant medical literature, and/or the like. The contents of the library may be indexed based on the specific characteristics of the computational models and simulations of cardiac arrhythmia. For instance, upon receiving the clinical data from the first user, the controller may be configured to index the clinical case by at least identifying, in the library, a computational model and simulations matching the clinical case and associating the corresponding clinical data with the matching computational model and simulations. A second user treating a patient for cardiac arrhythmia may, by querying the library based on patient data, gain access to not only matching computational simulations of cardiac arrhythmia but also relevant clinical data including, for example, patient anatomic information, diagnostic and/or treatment modalities, treatment parameters, treatment outcome, relevant medical literature, and/or the like.

In some example embodiments, non-patient specific computational models and simulations of cardiac arrhythmias included in the library may be enhanced using patient data collected during an electrophysiology (EP) study including, for example, action potential duration (APD) restitution data, conduction velocity restitution data, patient anatomical geometry, voltage mapping, intracardiac ultrasound data, transthoracic ultrasound data, conventional computed tomography (CT) data, cone-beam computed tomography (CT) data, positron-emission tomography (PET) scan data, fluoroscopy, magnetic resonance imaging data, patient demographics, cardiac activation pattern, regional conduction velocity, electrogram analysis, and/or the like. For example, the controller coupled with the library may be configured to modify, based at least on the patient data, one or more of the non-patient specific computational simulations included in the library. The modification may be performed in real time (or near real time) such that the modified library of computational simulations may be available when the patient is treated for their cardiac arrhythmia. For instance, localization of the source of a cardiac arrhythmia may be performed based on the modified library of computational simulations before ablation is performed at the source of the arrhythmia.

A computational model of a patient's anatomy, such as a computational representation of the patient's heart, may be used to provide supplemental information for a treatment, such as an ablation targeting the source of a cardiac arrhythmia in the patient's heart. Although the computational mapping result may visually identify the location of the source of cardiac arrhythmia within the computational model, the precise relationships between the computational model, the electroanatomic map of the heart, and the patient's actual anatomy may be unclear. As such, in some example embodiments, the computational model of the patient's anatomy may be aligned with the electroanatomic map, first, by tracking a position of one or more catheters, pacemaker leads, or implantable cardioverter defibrillator (ICD) leads relative to the patient's anatomy. Next, the location of an n-quantity of pacing sites at which a catheter, a pacemaker lead, or an implantable cardioverter defibrillator lead is positioned when applying one or more pacing impulses may be identified both in the computational model and in the electroanatomic map to provide n-quantity reference locations in order to align the computational model and the electroanatomic map. Finally, ablation may be performed at the source of the cardiac arrhythmia (e.g. ventricular fibrillation, as determined by the computational model mapping result), with positional reference to the position of the n-quantity of pacing sites identified in the computational simulation of the patient's anatomy.

FIG. 1 depicts a system diagram illustrating an example of a cardiac arrhythmia control system 100, in accordance with some example embodiments. Referring to FIG. 1, the cardiac arrhythmia control system 100 may include a data controller 110 and a data store 120. As shown in FIG. 1, the data controller 110 and the data store 130 may be communicatively coupled via a network 140. Moreover, FIG. 1 shows the data controller 110 as being communicatively coupled, via the network 140, to one or more clients including, for example, a first client 140a associated with a first user 145a, a second client 140b associated with a second user 145b, and/or the like. The first user 145a at the first client 140a and the second user 145b at the second client 140b may access, via the data controller 110, the contents of the data store 120, which may include a library 125 of computational simulations of cardiac arrhythmias. It should be appreciated that various techniques may be applied in order to securitize and/or anonymize the data that is stored and/or transmitted within the cardiac arrhythmia control system 100 including, for example, access control, encryption, blockchain, and/or the like.

In some example embodiments, the computational model and library 125 of computational simulations of cardiac arrhythmias may be enhanced with clinical data associated with clinical cases. To further illustrate, FIG. 2 depicts a flow diagram illustrating an example of a data flow 200 in the cardiac arrhythmia control system 100, in accordance with some example embodiments. Referring to FIGS. 1-2, the first user 145a at the first client 140a may send, to the data controller 110, clinical data associated with a clinical case including, as shown in FIG. 2, patient anatomic information 210a, diagnostic and/or treatment modalities 210b, treatment parameters 210c, clinical outcomes 210d, relevant medical literature 210e, and/or the like.

Referring again to FIG. 2, examples of patient anatomic information 210a may include cardiac geometry, scar and fibrosis locations, thorax anatomy and pathophysiology and/or the like. Patient anatomic information 210a may be captured in imaging studies obtained prior to and/or during the clinical case. Alternatively and/or additionally, patient anatomic information 210a may be captured during an electroanatomic mapping procedure. The patient anatomic information 210 may be loaded into the library 120 by loading, for example, raw imaging information including, for example, text files containing data of the patient information (e.g. output data files containing electrogram information from the electrophysiology recording system), intra-cardiac ultrasound images, transthoracic ultrasound images, computed tomography (CT) images, 4-dimensional computed tomography videos, magnetic resonance imaging (MRI) images, Myocardial Perfusion Imaging tests (MIBI), positron-emission tomography (PET) images, radiographs, and/or the like. Tomographic images may use a spectrum of interpretation from manual interpretation to automated 3-dimensional image creation and analysis.

Moreover, loading the patient anatomic information 210 into the library 120 may include importing digital information from 3-dimensional electroanatomic mapping systems such as geometry, catheter position, voltage maps, activation data, and analytic data. FIG. 3A depicts an example of a voltage map 310 indicating a relationship between voltage and scar/fibrosis density at various locations across a left ventricle and a right ventricle of a patient's heart. It should be appreciated that at least a portion of the patient anatomic information 210a may include annotations provided by the first user 145a. FIG. 3B depicts an example of a user interface 320 generated by the data controller 110. The user interface 320 may be displayed, for example, at the first client 140a in order to receive, from the first user 145a, one or more inputs corresponding to an interpretation of the geometry, orientation, voltage, activation, and analytic information from electroanatomic mapping systems.

Examples of diagnostic and/or treatment modalities 210b may include imaging technology (e.g., fluoroscopy, ultrasound, computed tomography (CT), magnetic resonance imaging (MRI), positron-emission tomography (PET) and/or the like), sheaths (e.g., pre-formed, steerable, and/or the like), mapping catheters (e.g., multi-electrode catheters), and ablation catheters (e.g., solid or irrigated, 8 mm or 3.5 mm tip size, and/or the like). In some example embodiments, the data controller 110 may generate a user interface including a dropdown menu (or another type of graphical user interface element) configured to enable the first user 145a to input the diagnostic and/or treatment modalities that were applied in the clinical case. Alternatively and/or additionally, the data controller 110 may receive, from the first user 145a, a scan identifying one or more products used during the clinical case including, for example, a product barcode (e.g. barcode from the box containing the ablation catheter used in the case), an image, and/or the like.

Examples of treatment parameters 210c may include parameters associated with ablation such as, for example, ablation power, location, duration of lesion placement, and the dimension and/or shape of the lesion. For example, digital information including one or more of the treatment parameters 210c may be exported from an electroanatomic mapping system and uploaded to the library 125. FIG. 3C depicts an example of an electroanatomic map showing, as dots, locations of ablation lesions. Alternatively and/or additionally, the data controller 110 may generate a user interface, which may be displayed at the first client 140a in order to receive, from the first user 145a, one or more inputs corresponding to an interpretation of the ablation power, location, duration of lesion placement, and the dimension and/or shape of the lesion.

Additional examples of treatment parameters 210c may include parameters associated with stereotactic ablative radiotherapy (SAbR) such as, for example, target contouring data, internal treatment volume (ITV), planning treatment volume (PTV), radiation dose, radiation energy/delivery time, avoidance structures, respiratory and cardiac motion gating parameters, patient positioning and/or restraining devices, use of paralyzing agents by anesthesia during therapy, pacemaker or implantable cardioverter-defibrillator (ICD) programming parameters, cardiac rhythm during therapy, arrhythmia mapping technology, associated computed tomography (CT) imaging data, associated magnetic resonance imaging (MRI) imaging data, associated ultrasound imaging and tracking data, medications, antiarrhythmic drug therapy, anticoagulation medical therapy, clinical outcomes, complications, and adverse events. For example, digital information including one or more of the treatment parameters 210c may be exported from an stereotactic ablative radiotherapy (SAbR) planning system and uploaded to the library 125. FIG. 3D depicts an example of planning software for stereotactic ablative radiotherapy (SAbR) showing target volumes, avoidance structures, and computed radiotherapy dosages. Alternatively and/or additionally, the data controller 110 may generate a user interface, which may be displayed at the first client 140a in order to receive, from the first user 145a, one or more inputs corresponding to an interpretation of the targeting contouring data, internal treatment volume (ITV), planning treatment volume (PTV), radiation dose, radiation energy/delivery time, avoidance structures, respiratory and cardiac motion gating parameters, patient positioning and/or restraining devices, use of paralyzing agents by anesthesia during therapy, pacemaker or implantable cardioverter-defibrillator (ICD) programming parameters, cardiac rhythm during therapy, arrhythmia mapping technology, associated computed tomography (CT) imaging data, associated magnetic resonance imaging (MRI) imaging data, associated ultrasound imaging and tracking data, medications, antiarrhythmic drug therapy, anticoagulation medical therapy, clinical outcomes, complications, and adverse events.

The clinical results 210d may include results associated with the ablation having the treatment parameters 210c including, for example, acute ablation success (e.g. ablation terminating the arrhythmia, ablation rendering the arrhythmia non-inducible, 6 month clinical outcome, and/or the like) and complications. Examples of the relevant medical literature 210e shown in FIG. 2 may include guidelines, clinical trials, expert opinions, and case reports that are relevant to the clinical case, and indexed according to the parameters of the computational model and arrhythmia simulation library (e.g. arrhythmia type, patient cardiac geometry and scar configuration, arrhythmia source location, etc.). The data controller 110 may generate a user interface including a dropdown menu (or another type of graphical user interface element) configured to enable the first user 145*a* to select one or more inputs from a selection of clinical results.

In some example embodiments, the data controller 110 may be configured to index the clinical data received from the first user 145*a* such that the clinical data may be accessible, for example, to the second user 145*b* at the second client 140*b*. The data controller 110 may be configured to index, based least on the computational simulations included in the library 125, the clinical data received from the first user 145*a* such that the clinical data is associated with a computational simulation that most closely matches the corresponding clinical case. For example, each computational simulation included in the library 125 may be associated with one or more characteristics including, for example, heart size, shape, presence or absence of structural heart disease, arrhythmia type, and/or the like. Upon receiving the clinical data associated with the clinical case from the first user 145*a,* the data controller 110 may be configured to compute, for each computational simulation in the library 125, a similarity score indicative of a closeness of a match between the respective characteristics of the clinical case and the computational model and simulation library 125. The clinical data associated with the clinical case may be indexed based on the computational model having a highest similarity score. That is, the clinical data associated with the clinical case may be associated with the computational model and/or simulations whose characteristics (e.g., heart size, shape, presence or absence of structural heart disease, arrhythmia type, and/or the like) most closely match those in the clinical case.

The contents of the simulation library 125, including computational model and/or simulations that have been enhanced with clinical data associated with matching clinical cases, may be accessible to the second user 145*b* at the second client 140*b*. For example, the second user 145*b* may query the library 125 in order to identify relevant clinical cases. In some example embodiments, the second user 145*b* may be treating a patient for a cardiac arrhythmia and may thus query the library 125 based on patient data including, for example, patient age, medical history, arrhythmia type, proposed treatment plan, and/or the like. The data controller 110 may respond to the query from the second user 145*b* by at least identifying one or more clinical cases included in the library 120 that match the parameters of the query from the second user 145*b*. Alternatively and/or additionally, instead of one or more specific clinical cases, the second user 145*b* may apply a collection of clinical cases from the library 120 as training data to train a machine learning model to perform a variety of cognitive tasks including, for example, determining the statistical probability of the arrhythmia source location, performing a probabilistic analysis of potential clinical outcomes associated with different treatment approaches (e.g. ablation lesion location and/or target volume, number, and pattern) for arrhythmia, and/or the like.

In some example embodiments, the machine learning model may include a neural network such as, for example, an autoencoder and/or the like. The machine learning model may be trained based on training data that includes clinical data from a large number of patient cases which may be collected and entered as input into the machine learning model. Training data may include patient demographic information, electrocardiographic (ECG) and vectorcardiographic (VCG) tracings, and ground truth labels including the identified arrhythmia source locations. Arrhythmia source locations may be further labeled with ablation site, size, volume, and technique (e.g., catheter ablation versus stereotactic ablative radiotherapy), and some ranking of the outcome (e.g. arrhythmia termination, acute ablation success, long-term ablation success, etc.). Moreover, the machine learning model may be trained to examine features present in the treatment approach for each patient (ablation lesion number, size, volume, configuration, therapy dose, etc.). Additionally, the machine learning model may be trained to determine a similarity metric between different clinical cases based on demographics, arrhythmia type, cardiac anatomy, etc. to determine relevance to both other training case data and/or future cases for comparison. When a user wants to utilize the trained machine learning model, the user may provide, as inputs to the trained machine learning model, a patient's electrocardiogram (ECG) or vectorcardiogram (VCG) as well as one or more patient characteristics and arrhythmia characteristics. The trained machine learning model may determine, based at least on the inputs, a statistical probability of the arrhythmia source location, and a probabilistic analysis of potential clinical outcomes associated with different treatment approaches (e.g. ablation lesion location, number, volume, configuration, therapy dose, etc.) for arrhythmia. In those instances, the data controller 110 may also be configured to identify, based at least on the output of the trained machine learning model, a selection of relevant clinical cases for case reference and procedural planning.

In some example embodiments, non-patient specific computational models and arrhythmia simulations included in the library 125 may be enhanced using patient data collected during an electrophysiology study (EPS) either in the electrophysiology laboratory, the radiation medicine suite, or operating room (OR) including, for example, action potential duration (APD) restitution data, conduction velocity restitution data, patient anatomical geometry, voltage mapping, intracardiac ultrasound data, transthoracic ultrasound data, conventional computed tomography data, cone-beam computed tomography data, 4-dimensional computed tomography date (4-D CT), magnetic resonance imaging (MRI) data, positron-emission tomography (PET) data, patient demographics, cardiac activation pattern, regional conduction velocity, electrogram analysis, and/or the like. For example, the data controller 110 may be configured to modify, based at least on the patient data, one or more of the non-patient specific computational models and arrhythmia simulations included in the library 125. In this example, the patient's left ventricular geometry and voltage map generated during an ablation case by the electroanatomic mapping system is exported to a USB memory stick and uploaded to the algorithm. The cardiac model is updated to include the information regarding left ventricular size, orientation, and the locations of normal tissue, scar tissue, and fibrosis. Next, previously-computed voltage solutions of cardiac arrhythmias are then incorporated into the updated cardiac model and the solutions run forward in time to compute the vectorcardiogram (VCG) library for the patient, with one or more VCG loops associated with each possible location of the cardiac arrhythmia source. The adjusted VCG library and associated location and other associated metadata are then returned to the clinical user to aid in the clinical case being performed. The modifications may be performed in real time (or near real time) such that the modified library 125 of computational simulations may be available when the patient is treated for their cardiac arrhythmia. For instance, localization of the source of ventricular fibrillation may be performed based on the modified library 125 of computational simulations before ablation is performed at the source of ventricular fibrillation.

FIG. 4 depicts a flowchart illustrating an example of a process 400 for modifying a library of non-patient specific computational simulations, in accordance with some example embodiments. As shown in Box A, the patient is brought into the electrophysiology laboratory, radiation medicine suite, or operating room, placed on the procedural table, and the procedure is begun (the electrophysiology study (EPS) environment is represented by the bottom portion of FIG. 4). Next, as described in Box B, a patient cardiac geometry is created using a combination of noninvasive techniques (e.g. transthoracic ultrasound, fluoroscopy, cone-beam computed tomography scan, magnetic resonance imaging, etc.) and/or invasive techniques (e.g. invasive electrophysiology catheters are placed in and maneuvered throughout the heart). The cardiac geometry is supplemented by APD restitution data, conduction velocity restitution data, voltage mapping data, intracardiac ultrasound data, patient demographic data [age, weight, height, ejection fraction], cardiac activation pattern, regional conduction velocity, and electrogram analysis. Next, these data are collected and securely exported to high-performance computing resources for analysis (area represented by the top of FIG. 4). In this environment, a pre-existing, non-patient-specific library of computational simulations of cardiac arrhythmias (Box 1) is rapidly scaled and adjusted according to the exported data (Box 2). In one example, the cardiac model is updated to include the information regarding left ventricular size, orientation, and the locations of normal tissue, scar tissue, and fibrosis. Next, previously-computed voltage solutions of cardiac arrhythmias are then incorporated into the updated cardiac model and the solutions run forward in time to compute the vectorcardiogram (VCG) library for the patient, with one or more VCG loops associated with each possible location of the cardiac arrhythmia source. As shown in Box 3, the adjusted library, voltage solutions, and arrhythmia source locations are returned to the local electrophysiology laboratory, radiation medicine suite, or operating room (OR) mapping system for patient arrhythmia mapping. Meanwhile in the clinical case (Box C), arrhythmia induction is attempted, if necessary. Arrhythmia electrograms are saved and exported for analysis. Diagnostic catheters are removed (if present) and either ablation catheters are placed within the heart, the stereotactic ablative radiotherapy (SAbR) plan is reviewed, or the surgical plan is evaluated. In Box D, arrhythmia source mapping is performed using the modified VCG library from Box 3. Arrhythmia source locations (the results of the computational mapping process) are displayed for interpretation of the physician. Informed by the mapping results, catheter ablation, stereotactic ablative radiotherapy, or surgical interruption of the arrhythmia sources is begun (Box E).

Referring to FIG. 4, the data controller 110 may be configured to modify the library 125 based on patient data collected during an electrophysiology (EP) study, as noted in FIG. 4, including patient demographics, and information derived by positioning one or more catheters in a patient's heart or from interrogation of an implanted pacemaker or an implantable cardioverter-defibrillator (ICD) in order to collect patient-specific data such as, for example, action potential duration (APD) restitution data, conduction velocity restitution data, patient anatomical geometry, voltage mapping, intracardiac ultrasound data, cardiac activation pattern, regional conduction velocity, electrogram analysis, and/or the like. The data controller 110 may modify the library 125, including by applying one or more patient-specific corrections, such that one or more of the computational simulations included in the library 125 better conform to patient specific characteristics.

To further illustrate, FIGS. 5A-C depict examples of data collected during an electrophysiology procedure, in accordance with some example embodiments. For example, FIG. 5A depicts an example of a result of single extrastimulus pacing in the atria, which may illustrate atrial action potential duration (APD) restitution and activation latency. The action potential duration (APD) restitution and activation latency shown in FIG. 5A may be used to determine the correct parameters for more accurate simulation of atrial arrhythmias within the patient's heart.

FIG. 5B depicts an example of endocardial geometries and voltage maps in a patient with nonischemic cardiomyopathy and ventricular arrhythmias. A significant amount of data relevant to the arrhythmia simulation process may be created during the electrophysiology mapping process using the 3-dimensional electroanatomic mapping system. For example, cardiac geometry and orientation may be obtained by moving electrophysiology catheters within the heart. The collection of points occupied by such catheters may be used to generate endocardial and epicardial surfaces of the heart shown, for example, in the endocardial geometries of the left (geometry on left side of FIG.) and right ventricles (geometry on right side of FIG.) shown in FIG. 5B.

FIG. 5C depicts an example of an intracardiac echocardiogram (ICE) image of a left ventricle, which the endocardial surface (bottom arrow) and a basket of catheter spline (top arrow). An intracardiac echocardiography (ICE) system or a transthoracic echocardiography system may collect dynamic, high resolution data regarding the thickness of cardiac walls, the position and thickness of various structures (e.g., papillary muscles, pulmonary vein, left and right atrial appendages), and the positions of other mapping and ablation catheters. The resulting echocardiographic images, such as the one shown in FIG. 5C, may therefore be used to further refine one or more non-patient specific computational simulations to conform to patient specific cardiac characteristics, as illustrated by the process 400 of FIG. 4 and described above.

In some example embodiments, patient data may be exported from the electroanatomic mapping system and transferred directly to the data controller 110. For example, patient geometry, voltage map, activation map, and electrogram morphology map may be saved a data file (e.g., to a universal serial bus (USB) memory stick, a compact disk (CD), a digital versatile disk (DVD), and/or the like) before being uploaded to the data controller 110. Alternatively, when direct export is not practicable, the data controller 110 may provide, for example, via a graphical user interface, a user-editable cardiac model and customizable tools for geometrical morphing and rotation, imposing a voltage and/or electrogram information onto the computational model and arrhythmia simulation, and indicating activation information. Global and/or regional information regarding the thickness of cardiac structure walls as well as the position and morphology of papillary muscles, pulmonary veins, and the left and right atrial appendages may also be incorporated into the model either by morphing the geometry or setting the wall thicknesses. It should be appreciated that various techniques may be applied in order to securitize and/or anonymize the data that is transmitted to and from the data controller 110 including, for example, access control, encryption, blockchain, and/or the like.

In some example embodiments, upon receiving the patient data, the data controller 110 may be configured to modify, based at least on the patient data, one or more computational models and arrhythmia simulations in the library 125 in real time or near real time. As noted, the modifications may include one or more patient specific corrections such that the computational simulations in the library 125 better conform to patient specific characteristics. For example, the data controller 110 may be configured to fit geometric data to a computational mesh such that the mesh relationships may be used to compute arrhythmia simulations for the patient of interest. The data controller 110 may also introduce, into the more patient specific model, voltage solutions of previously simulated rotors and focal sources. A computational simulation may then proceed forward in time to allow arrhythmia maturation and permutations to be recorded (e.g. for several seconds of simulated time). From the computational voltage solutions, the data controller 110 may compute and record vectorcardiography (VCG) data, which may be indexed to a source location of the cardiac arrhythmia. Alternatively and/or additionally, the computational renderings of voltage solutions may be performed and recorded as a resource for arrhythmia mapping and validation (e.g. the technology of U.S. Pat. No. 10,319,144 "Computational Localization of Fibrillation Sources").

The data controller 110 may, as noted, modify the library 125 in real time (or near real time) such that the modified library 125 of computational simulations may be available when the patient is treated for ventricular fibrillation. For example, the computed vectorcardiograms and associated source locations, along with the rendered voltage solutions may be encrypted and sent to the first client 140a and/or the second client 140b to at least enable the first user 145a and/or the second user 145b to determine the location of the patient's ventricular fibrillation before performing a treatment such as, for example, ablation at the source of ventricular fibrillation. It should be appreciated that the modified library 125 may enable the first user 145a and/or the second user 145b to perform a higher fidelity localization of the source of cardiac arrhythmia, thereby improving the clinical outcome of the treatment targeting the source of cardiac arrhythmia.

In some example embodiments, the data controller 110 may be configured to align the computational model used for arrhythmia simulation and computational arrhythmia mapping with a 3-dimensional electroanatomic map tracking the positions of one or more catheters relative to the patient's anatomy. This could be accomplished with the following workflow: First, an n-quantity of pacing maneuvers is performed within the patient's heart using either a steerable catheter or pacing electrodes of a pacemaker or implantable cardioverter-defibrillator. Next, the sites of pacing are recorded within the patient's heart using a 3-dimensional electroanatomic mapping system. Next, the n-quantity sites at which pacing was performed may be identified in the computational arrhythmia mapping system by analyzing each of the paced QRS complexes (e.g. the vectorcardiogram from the paced QRS complexes is computed) and comparing with the library of simulated pacing vectorcardiograms. The vectorcardiogram with the highest similarity score would provide information regarding the location of the site of pacing for that heartbeat. Next, the computational model and electroanatomic mapping system geometry are combined, either by export of the electroanatomic mapping geometry into the computational model arrhythmia mapping system, export of the computational model geometry into the electroanatomic mapping system, or conceptually, by using, for example, a least-squares fitting algorithm to best superimpose the positions of the n-quantity pacing locations. Ablation may then be performed at the source of the cardiac arrhythmia, as referenced to the position of the n-quantity of pacing sites identified in the computational simulation of the patient's anatomy.

FIG. 6A depicts an example of a computational model 600 with the location of a source of ventricular fibrillation shown, in accordance with some example embodiments. The computational simulation 600 shown in FIG. 6A may be a "heat map" indicating a location of a source of cardiac arrhythmia in a patient. The example of the computational model and mapping solution 600 shown in FIG. 6A may be generated, for example, from the clinical 12-lead electrocardiogram (ECG) data of the arrhythmia of interest and its computed vectorcardiogram, matched to the simulated vectorcardiogram library of arrhythmia simulations. Although the computational model 600 shows the location of the source of cardiac arrhythmia, a precise relationship between the patient's anatomy and the geometry of the computational simulation 600 may be lacking. As such, the computational model and mapping solution 600 alone may not provide sufficient actionable data to a clinician treating the patient for cardiac arrhythmia.

In order to provide a precise location of the source of cardiac arrhythmia relative to the patient's anatomy, the data controller 110 may be configured to align the computational simulation of a patient's anatomy, such as computational model and mapping output 600 shown in FIG. 6A, may be aligned with an electroanatomic mapping 610 shown in FIG. 6B. Referring to FIG. 6B, the electroanatomic mapping 610 may track a position of one or more catheters (indicated by the top arrows) or the pacing electrodes of the pacemaker or implantable cardioverter-defibrillator (ICD) relative to the patient's anatomy (e.g., the left ventricle) as well as areas of low voltage (indicated by the bottom arrows). As such, in some example embodiment, the data controller 110 may determine, based at least on an electroanatomic mapping, the location of an n-quantity (e.g., three or more) of pacing sites at which a catheter is positioned or pacing electrodes of a pacemaker or implantable cardioverter-defibrillator are located when applying one or more pacing impulses. To further illustrate, FIG. 6C depicts an example of an electroanatomic map 620 including pacing sites (indicated by the arrows). The data controller 110 may further determine, in the computational mapping solution 600, the location of the same n-quantity of pacing sites. FIG. 6D shows the computational model 600 in which the n-quantity of pacing sites are indicated by small white dots (noted by arrows). Notably, as shown in FIG. 6D, the location of the source of cardiac arrhythmia may be referenced relative to the location of the n-quantity of pacing sites. As described above, the computational model geometry may be aligned with the 3-dimensional electroanatomic mapping system geometry (or vice-versa) using a 3-dimensional least-squares fitting algorithm referencing the locations of the n-quantity pacing locations. As a result of this alignment process, an updated FIG. 6D could be generated and displayed to the user, and targeted therapy may be more precisely delivered to the site of interest from FIG. 6D (labelled "source of cardiac arrhythmia").

In some example embodiments, the location of the source of cardiac arrhythmia may be translated to the electroanatomic mapping system using a prolate spheroidal coordinate system that serves as a reference system for cardiac chambers. FIGS. 7A-B depicts a prolate spheroidal coordinate system 700, in accordance with some example embodiments. As shown in FIGS. 7A-B, a location within the prolate spheroidal coordinate system 700 may be expressed as the tuple σ, τ, and φ, wherein σ=cosh (μ) and τ=cos (ν).

Once the locations of the n-quantity of pacing sites are known in the computational simulation 600 and the electro-anatomic map 620, the positions of the n-quantity of pacing sites may be used to align, using a transformative matrix A, the respective reference coordinate systems of the computational simulation 600 and the electroanatomic map 620. The location of the source of the cardiac arrhythmia may be further defined based on the locations of the n-quantity of pacing sites and be plotted, in the prolate spheroidal coordinate system 700, with the tuple $\sigma_{source}$, $\tau_{source}$, and $\varphi_{source}$. The position of the source of cardiac arrhythmia relative to the n-quantity of pacing sites may be actionable data to a clinician treating the patient for cardiac arrhythmia. For example, the computational model from FIG. 6D may be aligned with electroanatomic mapping geometry from FIG. 6C using a least-squares fitting process. The geometry to be fitted could be transformed to the reference geometry via a process combining rotation, scaling, and translation (e.g. within the prolate spheroidal coordinate system, for example). A new image of the combined and aligned data (an "updated" FIG. 6D) could be generated and displayed to the user to allow precise targeting of the arrhythmia source. In particular, treatments including, for example, ablation, targeted gene therapy, stereotactic ablative radiotherapy (e.g., gamma radiation, proton beam), and surgical intervention, may be performed at the locations identified as the source of cardiac arrhythmia. For example, FIG. 8A depicts left ventricle and right ventricle geometries with multiple ablation sites where radiofrequency, cryogenic temperatures, ultrasound, and/or stereotactic ablative radiotherapy may be applied to alleviate the cardiac arrhythmia by disrupting and/or eliminating the erratic electric signals causing the dyssynchronous heart contractions associated with cardiac arrhythmia. FIG. 8B depicts an example of the delivery of stereotactic ablative radiotherapy (SAbR) in a patient with refractory ventricular arrhythmias.

FIG. 9A depicts a flowchart illustrating an example of a process 900 for enhancing a library of computational simulations with data associated with clinical cases, in accordance with some example embodiments. Referring to FIGS. 1-2, 3A-C, and 9A, the process 900 may be performed by the data controller 110 in order to supplement one or more of the computational simulations included in the library 125 with clinical data associated with clinical cases.

At 902, the data controller 110 may receive, from the first user 145a, clinical data associated with a clinical case. For example, the data controller 110 may receive, from the first user 145a at the first client 140a, clinical data associated with a clinical case that includes, for example, patient anatomic information, diagnostic and/or treatment modalities, treatment parameters, treatment outcome, relevant medical literature, and/or the like.

At 904, the data controller 110 may store, in the library 125, at least a portion of the clinical data including by associated with the clinical data with a computational simulation having characteristics that most closely match the characteristics of the clinical case. For example, upon receiving the clinical data associated with the clinical case, the data controller 110 may compute, for each computational simulation in the library 125, a similarity score indicative of a closeness of a match between the respective characteristics of the clinical case and the computational simulations in the library 125. The clinical data associated with the clinical case may be indexed based on the computational simulation having a highest similarity score. For instance, the clinical data associated with the clinical case may be associated with the computational simulation whose characteristics (e.g., heart size, shape, presence or absence of structural heart disease, arrhythmia type, and/or the like) most closely match those in the clinical case.

At 906, the data controller 110 may respond to a query from the second user 145b by at least sending, to the second user 145b, data from the library 125 including at least a portion of the clinical data associated with the clinical case. For example, the second user 145b may be treating a patient for cardiac arrhythmia and may thus query the library 125 based on patient data including, for example, patient age, medical history, proposed treatment plan, and/or the like. The data controller 110 may respond to the query from the second user 145b by at least identifying one or more clinical cases included in the library 120 that match the parameters of the query from the second user 145b. Alternatively and/or additionally, instead of one or more specific clinical cases, the second user 145b may apply a collection of clinical cases from the library 120 as training data to train a machine learning model to perform a variety of cognitive tasks including, for example, determining the statistical probability of the arrhythmia source location, performing a probabilistic analysis of potential clinical outcomes associated with different treatment approaches (e.g. ablation lesion location, number, and pattern) for arrhythmia, and/or the like.

In some example embodiments, the machine learning model may include a neural network such as, for example, an autoencoder and/or the like. The machine learning model may be trained based on training data that includes clinical data from a large number of patient cases which may be collected and entered as input into the machine learning model. Training data may include patient demographic information, electrocardiographic (ECG) and vectorcardiographic (VCG) tracings, and ground truth labels including the identified arrhythmia source locations. Arrhythmia source locations may be further labeled with ablation site, size, technique, internal targeting volume (ITV), planning targeting volume (PTV), ablation energy dose, and some ranking of the outcome (e.g. arrhythmia termination, acute ablation success, long-term ablation success, etc.). Moreover, the machine learning model may be trained to examine features present in the treatment approach for each patient (ablation lesion, number, size, configuration, internal targeting volume (ITV), planning targeting volume (PTV), ablation energy dose, etc.). Additionally, the machine learning model may determine a similarity metric between different clinical cases based on demographics, arrhythmia type, cardiac anatomy, etc. to determine relevance to both other training case data and/or future cases for comparison. When a user wants to utilize the trained machine learning model, the user may provide, as inputs to the trained machine learning model, a patient's electrocardiogram (ECG) or vectorcardiogram (VCG) as well as one or more patient characteristics and arrhythmia characteristics. The trained machine learning model may determine, based at least on the inputs, a statistical probability of the arrhythmia source location, and a probabilistic analysis of potential clinical outcomes associated with different treatment approaches (e.g. ablation lesion location, number, and pattern) for arrhythmia. Accordingly, the data controller 110 may also be configured to identify, based at least on the output of the trained machine learning model, a selection of relevant clinical cases for case reference and procedural planning.

FIG. 9B depicts a flowchart illustrating an example of a process 920 for modifying a library of computational simulations, in accordance with some example embodiments. Referring to FIGS. 1, 4, 5A-C, and 9B, the process 920 may be performed by the data controller 110 in order to modify one or more computational simulations in the library 125 to better conform to patient specific characteristics.

At 922, the data controller 110 may receive patient data collected during an electrophysiology study in either the electrophysiology laboratory, radiation medicine suite, or operating room. In some example embodiments, the data controller 110 may receive patient data collected during an electrophysiology (EP) study including, for example, action potential duration (APD) restitution data, conduction velocity restitution data, patient anatomical geometry, voltage mapping, intracardiac ultrasound data, patient demographics, cardiac activation pattern, regional conduction velocity, electrogram analysis, and/or the like.

At 924, the data controller 110 may modify, based at least on the patient data, one or more computational simulations included in the library 125. In some example embodiments, the data controller 110 may modify, based at least on the patient data, one or more of the non-patient specific computational simulations included in the library 125 such that the one or more non-patient specific computational simulations better conform to patient specific characteristics. These modifications may be performed in real time (or near real time) such that the modified library 125 of computational simulations may be available when the patient is treated for cardiac arrhythmia.

At 926, the data controller 110 may send, to the first client 140*a* and/or the second client 140*b*, the modified computational simulations to enable the first user 145*a* and/or the second user 145*b* to determine, based at least on the modified computational simulations, a location of a source of cardiac arrhythmia and perform one or more treatments at the location of the source of cardiac arrhythmia. For example, the first user 145*a* and/or the second user 145*b* may perform, based at least on the modified computational simulations, a higher fidelity localization of the source of cardiac arrhythmia. Accordingly, the outcome of subsequent treatments performed at the source of cardiac arrhythmia may be improved due to the higher fidelity localization of the source of cardiac arrhythmia.

FIG. 9C depicts a flowchart illustrating an example of a process 930 for aligning a computational simulation with an electroanatomic mapping, in accordance with some example embodiments. Referring to FIGS. 1, 6A-D, 7A-B, 8, and 9C, the process 930 may be performed by the data controller 110 in order to further localize the source of cardiac arrhythmia.

At 932, the data controller 110 may identify, in an electroanatomic map, the location of an n-quantity of pacing sites at which a catheter is positioned when applying one or more pacing impulses. For example, as shown in FIG. 6C, the data controller 110 may identify, in the electroanatomic map 620, one or more pacing sites.

At 934, the data controller 110 may identify, in a computational simulation of a patient's anatomy, the location of the n-quantity of pacing sites. For instance, as shown in FIG. 6D, the data controller 110 may further identify, in the computational simulation 600, the location of the same n-quantity of pacing sites.

At 936, the data controller 110 may align, based at least on the location of the n-quantity of pacing sites, the electroanatomic map and the computational simulation of the patient's anatomy such that the location the source of cardiac arrhythmia is indicated by the location of the n-quantity of pacing sites. In some example embodiments, the data controller 110 may align the electroanatomic map 620 and the computational simulation 600 based on the location of the n-quantity of pacing sites. For example, once the locations of the n-quantity of pacing sites are known in the computational simulation 600 and the electroanatomic map 620, the positions of the n-quantity of pacing sites may be used to align, using a transformative matrix A, the respective reference coordinate systems of the computational simulation 600 and the electroanatomic map 620. Using, for example, a least-squares fitting algorithm incorporation rotation, translation, and scaling, alignment of the electroanatomic map 620 and the computational simulation 600 may be accomplished. Thus, the location of the source of cardiac arrhythmia may be further defined based on the locations of the n-quantity of pacing sites.

At 938, the data controller 110 may generate a user interface displaying the location the source of cardiac arrhythmia relative to the location of the n-quantity of pacing sites. As noted, the position of the source of cardiac arrhythmia relative to the n-quantity of pacing sites may be actionable data to a clinician treating the patient for cardiac arrhythmia. Accordingly, the data controller 110 may provide this information to the first user 145*a* and/or the second user 145*b* including, for example, by generating a user interface displaying location the source of cardiac arrhythmia relative to the location of the n-quantity of pacing sites. Treatments including, for example, ablation, targeted gene therapy, stereotactic ablative radiotherapy (e.g., gamma radiation, proton beam), and surgical intervention, may be performed at the locations identified as the source of the cardiac arrhythmia. For example, as shown in FIG. 8, the first user 145*a* and/or the second user 145*b* may perform treatments at the location of the source of the cardiac arrhythmia to alleviate the arrhythmia by disrupting and/or eliminating the erratic electric signals causing the abnormal heart contractions associated with arrhythmia.

FIG. 10 depicts a block diagram illustrating a computing system 1000, in accordance with some example embodiments. Referring to FIGS. 1 and 10, the computing system 1000 can be used to implement the data controller 110 and/or any components therein.

As shown in FIG. 10, the computing system 1000 can include a processor 1010, a memory 1020, a storage device 1030, and input/output device 1040. The processor 1010, the memory 1020, the storage device 1030, and the input/output device 1040 can be interconnected via a system bus 1050. The processor 1010 is capable of processing instructions for execution within the computing system 1000. Such executed instructions can implement one or more components of, for example, the data controller 110. In some implementations of the current subject matter, the processor 1010 can be a single-threaded processor. Alternately, the processor 1010 can be a multi-threaded processor. The processor 1010 is capable of processing instructions stored in the memory 1020 and/or on the storage device 1030 to display graphical information for a user interface provided via the input/output device 1040.

The memory 1020 is a computer readable medium such as volatile or non-volatile that stores information within the computing system 1000. The memory 1020 can store data structures representing configuration object databases, for example. The storage device 1030 is capable of providing persistent storage for the computing system 1000. The storage device 1030 can be a floppy disk device, a hard disk device, an optical disk device, or a tape device, or other suitable persistent storage means. The input/output device

1040 provides input/output operations for the computing system 1000. In some implementations of the current subject matter, the input/output device 1040 includes a keyboard and/or pointing device. In various implementations, the input/output device 1040 includes a display unit for displaying graphical user interfaces.

According to some implementations of the current subject matter, the input/output device 1040 can provide input/output operations for a network device. For example, the input/output device 1040 can include Ethernet ports or other networking ports to communicate with one or more wired and/or wireless networks (e.g., a local area network (LAN), a wide area network (WAN), the Internet).

In some implementations of the current subject matter, the computing system 1000 can be used to execute various interactive computer software applications that can be used for organization, analysis and/or storage of data in various (e.g., tabular) format. Alternatively, the computing system 1000 can be used to execute any type of software applications. These applications can be used to perform various functionalities, e.g., planning functionalities (e.g., generating, managing, editing of spreadsheet documents, word processing documents, and/or any other objects, etc.), computing functionalities, communications functionalities, and/or the like. The applications can include various add-in functionalities or can be standalone computing products and/or functionalities. Upon activation within the applications, the functionalities can be used to generate the user interface provided via the input/output device 1040. The user interface can be generated and presented to a user by the computing system 1000 (e.g., on a computer screen monitor, etc.).

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to as programs, software, software applications, applications, components, or code, include machine instructions for a programmable processor, and can be implemented in a high-level procedural and/or object-oriented programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively, or additionally, store such machine instructions in a transient manner, such as for example, as would a processor cache or other random-access memory associated with one or more physical processor cores.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A system, comprising:

at least one processor; and at least one memory including program code which when executed by the at least one processor provides operations comprising:

generating a library of computational simulations that are each associated with characteristics including a source location of an arrhythmia and a simulated cardiogram by, for each computational simulation, simulating voltage solutions of a heart based on at least some of the characteristics, generating a simulated cardiogram based on the simulated voltage solutions, and associating with the computational simulations the simulated cardiogram;

for each of a plurality of clinical cases, receiving clinical data associated with that clinical case, the clinical data including a clinical cardiogram; and indexing, based at least on a first plurality of characteristics associated with that clinical data, the clinical case, the indexing includes associating at least a portion of the clinical data of that clinical case with a computational simulation of an arrhythmia of the library, the indexing based on one or more characteristics matching one or more of the first plurality of characteristics, the matching one or more of characteristics include matching the clinical cardiogram and the simulated cardiogram of that computational simulation;

receiving a query that includes patient characteristics associated with a patient that include a patient cardiogram; and responding to the query by providing at least a portion of the clinical data associated with an indexed clinical case associated with a simulated cardiogram matching the patient cardiogram and providing an indication of the source location of the computational simulation to which the indexed clinical case is indexed;

wherein the patient is treated with an ablation to treat an arrhythmia of the patient based on the provided portion of the indexed clinical case and the provided indication of the source location.

2. The system of claim 1, wherein the clinical data includes patient anatomic information, diagnostic and/or treatment modalities, treatment parameters, treatment outcome, and medical literature.

3. The system of claim 1, wherein the first plurality of characteristics and the patient characteristics include patient demographics, medical history, and treatment plan.

4. The system of claim 1, wherein the indexing includes determining, for each of a plurality of computational simulations of arrhythmias included in a library, a similarity score indicative of a closeness of match between the first plurality of characteristics associated with the clinical data and the patient characteristics associated with each of the plurality of computational simulations, and wherein the indexing further includes associating at least the portion of the data with one of the plurality of computational simulations having a highest similarity score.

5. A method, comprising:
under control of a system having a processor and a memory,
accessing a library generated based on computational simulations, each computational simulation associated with library characteristics that include a library cardiogram generated from that computational simulation, the library characteristics including a source location of an arrhythmia;
for each of a plurality of first users,
receiving clinical data associated with a clinical case of that first user, the clinical data including a clinical cardiogram; and
indexing, based at least on a first plurality of characteristics associated with the clinical data, the clinical case, the indexing includes associating at least a portion of the clinical data of that clinical case with a computational simulation of an arrhythmia of the library, the indexing based on one or more library characteristics matching one or more of the first plurality of characteristics, the matching one or more of characteristics include a cardiogram;
receiving a query that includes patient characteristics associated with a patient that include a patient cardiogram; and
responding to the query by providing at least a portion of the clinical data associated with an indexed clinical case associated with a library cardiogram matching the patient cardiogram and providing the source location associated with the computational simulation associated with the indexed clinical case; and
performing an ablation to treat an arrhythmia of the patient based on the provided source location.

6. The method of claim 5, wherein the clinical data includes patient anatomic information, diagnostic and/or treatment modalities, treatment parameters, treatment outcome, and medical literature.

7. The method of claim 5, wherein the first plurality of characteristics and the patient characteristics include patient demographics, medical history, and treatment plan.

8. The method of claim 5, wherein the indexing includes determining, for each of a plurality of computational simulations of arrhythmias included in a library, a similarity score indicative of a closeness of match between the first plurality of characteristics associated with the clinical data and the patient characteristics associated with each of the plurality of computational simulations, and wherein the indexing further includes associating at least the portion of the data with one of the plurality of computational simulations having a highest similarity score.

9. A system, comprising:
at least one processor; and
at least one memory including program code which when executed by the at least one processor provides operations comprising:
generating a library of computational simulations that are each associated with cardiac characteristics that include a source location of an arrhythmia and a simulated cardiogram by, for each computational simulation, generating a simulated cardiogram based on simulated voltage solutions of a computational simulation of a heart having those cardiac characteristics and associating the simulated cardiogram with the computational simulation;
receiving patient data collected during an electrophysiology study;
modifying, based at least on the patient data, one or more of the computational simulations;
determining, based at least on the modified one or more computational simulations, a source location of an arrhythmia; and
providing an indication of the source location of the arrhythmia to inform treatment based on the patient data
wherein the patient is treated with an ablation based on the indicated source location.

10. The system of claim 9, wherein the patient data includes at least one of an action potential duration restitution data, conduction velocity restitution data, patient anatomical geometry, voltage mapping, intracardiac ultrasound data, transthoracic ultrasound data, cone-beam computed tomography data, fluoroscopy data, patient demographics, cardiac activation pattern, regional conduction velocity, and electrogram characteristics.

11. The system of claim 9, wherein the modifying includes applying, to the one or more computational simulations, a patient-specific enhancement including at least one of a geometrical morphing and/or rotating, imposing a voltage and/or electrogram information onto the one or more computational simulations, indicating an activation information, adding global and/or regional information regarding a thickness of cardiac structure walls, and incorporating global and/or geographical information regarding the position and morphology of papillary muscles, pulmonary veins, and/or left and right atrial appendages.

12. The system of claim 9, wherein the modifying is performed in real time or near real time, and wherein the modified one or more computational simulations of arrhythmia are returned to a user for clinical use.

13. The system of claim 9, wherein the one or more computational simulations are non-patient specific computational simulations.

14. The system of claim 9, further comprising:
initiating, based at least on one or more arrhythmia solutions associated with the modified one or more computational simulations of arrhythmia, an arrhythmia simulation to generate a patient-tailored arrhythmia cardiogram library for use in a computational arrhythmia mapping process.

* * * * *